US009681238B2

(12) United States Patent
Chan et al.

(10) Patent No.: US 9,681,238 B2
(45) Date of Patent: Jun. 13, 2017

(54) SYSTEM AND METHOD FOR AUDITORY CANAL MEASURING, FACIAL CONTOURING

(71) Applicants: Benjamin Chan, Markham (CA); Stephen Kun Chung Ho, Toronto (CA)

(72) Inventors: Benjamin Chan, Markham (CA); Stephen Kun Chung Ho, Toronto (CA)

( * ) Notice: Subject to any disclaimer, the term of this patent is extended or adjusted under 35 U.S.C. 154(b) by 0 days.

(21) Appl. No.: 14/784,646

(22) PCT Filed: Apr. 15, 2014

(86) PCT No.: PCT/CA2014/000350
§ 371 (c)(1),
(2) Date: Oct. 15, 2015

(87) PCT Pub. No.: WO2014/169372
PCT Pub. Date: Oct. 23, 2014

(65) Prior Publication Data
US 2016/0088410 A1 Mar. 24, 2016

Related U.S. Application Data

(60) Provisional application No. 61/812,101, filed on Apr. 15, 2013.

(51) Int. Cl.
*G06K 9/00* (2006.01)
*H04R 25/00* (2006.01)
(Continued)

(52) U.S. Cl.
CPC ............. *H04R 25/70* (2013.01); *A61B 6/032* (2013.01); *A61B 6/4085* (2013.01);
(Continued)

(58) Field of Classification Search
CPC .. G06T 7/00; G06T 17/00; A61B 6/00; G06K 9/00
(Continued)

(56) References Cited

U.S. PATENT DOCUMENTS 7,893,934 B2 * 2/2011 Gan .......................... A61B 5/12
345/419
9,301,056 B2 * 3/2016 Sohn .................... H04R 25/305
(Continued)

FOREIGN PATENT DOCUMENTS

WO 2013086116 A1 6/2013

OTHER PUBLICATIONS

WIPO, International Search Report and Written Opinion for PCT Application No. PCT/CA2014/000350 dated Jul. 16, 2014.
(Continued)

*Primary Examiner* — Abolfazl Tabatabai
(74) *Attorney, Agent, or Firm* — Heer Law; Christopher O. Heer

(57) ABSTRACT

A computer-implemented method and system is provided, comprising extracting measurements of at least one auditory canal from at least one computerized imaging scan of the at least one auditory canal devoid of physical measurement aids; determining eligibility for at least one auditory canal device at least partly by comparing the measurements of the at least one auditory canal with predetermined measurements of the at least one auditory canal device; and providing an indication of the eligibility determination contemporaneously with the measurement extracting.

20 Claims, 30 Drawing Sheets

(51) Int. Cl.
| | |
|---|---|
| *A61B 6/00* | (2006.01) |
| *A61B 6/03* | (2006.01) |
| *G06T 5/50* | (2006.01) |
| *G06T 17/00* | (2006.01) |
| *G06T 7/35* | (2017.01) |
| *A61B 5/00* | (2006.01) |

(52) U.S. Cl.
CPC ............ *A61B 6/4476* (2013.01); *A61B 6/501* (2013.01); *A61B 6/5217* (2013.01); *A61B 6/563* (2013.01); *G06T 5/50* (2013.01); *G06T 7/35* (2017.01); *G06T 17/00* (2013.01); *H04R 25/652* (2013.01); *G06T 2200/04* (2013.01); *G06T 2207/10081* (2013.01); *G06T 2207/20221* (2013.01); *G06T 2207/30052* (2013.01); *H04R 2225/023* (2013.01); *H04R 2225/025* (2013.01); *H04R 2225/77* (2013.01); *H04R 2225/81* (2013.01)

(58) Field of Classification Search
USPC ......... 382/128–134; 378/4, 8, 901; 600/407, 600/410, 411, 425, 427, 25, 26, 27, 559
See application file for complete search history.

(56) References Cited

U.S. PATENT DOCUMENTS

| | | |
|---|---|---|
| 2008/0143712 A1 | 6/2008 | McBagonluri et al. |
| 2010/0318208 A1 | 12/2010 | Schiller et al. |
| 2011/0066058 A1* | 3/2011 | Singh .................... A61B 5/085 600/529 |

OTHER PUBLICATIONS

Dammann et al., Computer-aided Surgical Planning for Implantation of Hearing Aids Based on CT Data in a VR Environment, RadioGraphics, Jan.-Feb. 2001, vol. 21, No. 1, pp. 183-190.

* cited by examiner

SYSTEM AND METHOD FOR AUDITORY CANAL MEASURING, FACIAL CONTOURING

CROSS-REFERENCE TO RELATED APPLICATION(S)

This application claims all benefit, including priority, of U.S. Provisional Patent Application Ser. No. 61/812,101, filed 15 Apr. 2013 and entitled SYSTEM AND METHOD FOR AUDITORY CANAL MEASURING, the entire contents of which is incorporated herein by reference, in its entirety.

FIELD OF THE INVENTION

This invention relates generally to medical imaging. This invention relates more particularly to imaging aspects of a person.

BACKGROUND OF THE INVENTION

Various technologies exist for custom fitting a hearing aid for a patient. Variations of hearing aids exist including behind the ear ("BTE") with a custom ear mold attached towards the hearing aid, and custom products which includes, in the canal (ITC) as well completely in the canal ("CIC"). In order to custom fit these, or other types of hearing aids, an impression is made of the patient's external auditory meatus ("EAM"), the ear canal, or auditory canal extending from the patient's external ear opening in the pinna (the visible part of the ear that resides outside of the head) to the tympanic membrane (eardrum). An ear impression is a physical replica of a portion of the ear created by injecting impression material into the ear canal and external ear cavities, such as the concha and helix areas of the ear. Impression materials may include liquid-powder (ethyl methacrylate) and silicone-based materials.

There is a risk to the patient any time foreign material is introduced into the auditory canal. In particular, there is a risk of damaging the tympanic membrane located in the auditory canal should the tympanic membrane be contacted by the impression materials. In addition, impression materials may cause allergic reactions in some patients. Contacting, perforating, or otherwise damaging the tympanic membrane can cause considerable pain for the patient, and may increase chances of the patient developing a middle ear infection. In order to address the risk of impression materials contacting the tympanic membrane, an oto-block may be inserted into the ear in advance of the impression materials. An oto-block is typically a cotton ball or sponge attached to a thread that is placed into the auditory canal to prevent impression material from going further into the ear canal than required while conducting an ear mold impression. The oto-block size is important to ensure that the impression material does not pass the oto-block, but oto-blocks are not always completely effective at blocking impression materials.

Another problem is that in order to obtain a usable impression, the impression materials must solidify before they may be removed from the auditory canal. As the impression material solidifies, pressure in the patient's auditory canal increases. Although this may cause discomfort in patients of all ages, children may be particularly susceptible to pain or discomfort while the impression material solidifies. The patient must remain at least relatively stable while the oto-block is being inserted, while the impression material is being inserted, while the impression material solidifies, and while the impression material is being removed. Any patient, but particularly children, may resist any of these actions and may have to be restrained or assisted by a clinician, parent, guardian. Furthermore, once the oto-block is in place, it is important that the patient not move or remove the oto-block.

A further problem is that it is preferable to treat auditory disorders as early in a person's life as possible once diagnosed. However, certain conditions existing in a patient's auditory canal may delay the making of an impression. Infant, toddler, and preschool children are prone to ear infection during childhood development, particularly between the ages of 6 months and 3 years. Not only can impression material increase a child's risk of developing an ear infection, but an existing infection may need to be treated prior to an impression being taken. Other problems occurring in young or older children may include inflammation and fluid or cerumen (earwax) build-up in the middle ear or external ear. Any of these conditions may prevent an ear mold impression from being taken until the condition is treated, either because making an impression would be too painful while under the effects of the condition, or the condition may cause constriction or other deformation in the shape the auditory canal for the purposes of impression. Delaying the impression process may be problematic for children since doing so would delay the overall timeframe for treating the child's cognitive auditory issues or deficiencies. Especially in children, cognitive auditory treatment is most effective when performed early as plasticity development differs from children and adults. Where a child receives appropriate auditory amplification through treatment, it will have a large impact towards central auditory brain development, critical at least during the first two years of a child's life. If the child has hearing loss during this period, the child is likely to have a delayed ability to adapt when compared with children without cognitive auditory disorders. A child with hearing loss should therefore receive cognitive auditory treatment as soon as possible. With early treatment, the child's auditory brain development is able to revert back to normal or near normal central pathway development. With adults, once hearing loss progresses over a long period without treatment, the ability to alter near normal central auditory brain development will require a significantly greater amount of time. This process may be referred to as the acclimatization period, which has been shown to be faster in children than in adults. During this period, adults may require time adjusting towards extrinsic signals, or amplification, which has altered the central auditory pathways towards the brain. However, an adult with acquired hearing loss should already have prior knowledge and understanding of language, which would assist in allowing the adult to understand speech intelligibility without having all audible sounds towards speech.

A current preferred practice for making an ear impression may involve several items including: an otoscope with speculum; an ear light with removable tip; an oto-block with thread; a mixing bowl or wax pad; a spatula; blunt-end tweezers; blunt-end scissors; bite-blocks; a syringe or impression gun; and a variety of impression materials. Traditionally, the steps of inserting an oto-block, mixing impression materials, and removing the ear mold impression after solidification require at least 10 minutes for a single ear. In addition, depending on the density and shore of the ear mold impression, the traditional method requires clinicians to have good manual dexterity to insert impression material if an impression gun is not available. Coordination and release of impression material into the EAM all the way towards the pinna is also required to achieve an airtight seal. Pressure created from the impression material solidifying increases the risk of perforating the tympanic membrane. Recovery time from a perforated tympanic membrane may be long and painful.

In the current preferred practice, once the impression has solidified and is removed from the patient, the impression may be sent by mail to the hearing aid manufacturer for development of a corresponding prosthetic product using the replicated impression. Alternatively, a 3D image of the impression may be created and transmitted to the hearing aid manufacturer. The 3D image may be created by scanning the impression using an optical coherence tomography device ("OCT"). An OCT device is a non-invasive imaging system which may be used to collect high-resolution, three-dimensional tissue images from beams of light. This is a multi-step process by first taking the physical impression of the EAM and secondly, taking the EAM impression to the OCT to create a 3D imaging file from the impression.

Another problem with the current practice of creating an ear mold using impression materials is that errors may exist including incorrect technique used during measurement and improper use of the impression tools. Often, these errors will not be identified until after the hearing aid device is produced and an attempt to fit the device in the patient's ear is made.

An invisible-in-the-canal ("IIC") device may be designed to be positioned millimeters away from the tympanic membrane in the EAM. If a patient is subjected to the traditional method of ear mold impression, the impression materials reach only millimeters away from the tympanic membrane, which can be very uncomfortable for the patient. Discomfort is not the only issue, as an ear impression that extends 10-12 mm beyond the second bend in the EAM is required for an accurate and comfortable fit of an IIC device. While no special equipment is necessarily required for IIC impressions, instrumentation to illuminate and view the ear canal beyond the second bend is valuable. Furthermore, silicone impressions may be taken with a high flow and a low viscosity material will typically fill the entire canal accurately and completely. A flattened oto-block may also be placed deep in the canal, very near the tympanic membrane.

Cepholometric radiography may also be used. A radiographic marker is placed in the patient's EAM and mounted on the ear post in the EAM. An ear canal blocker is also required.

A material socket may be used and a radiographic marker placed in the EAM.

Infrared light technology may be used in order to generate a 3D image of the EAM. Excellent positioning of the probe head is required in order to obtain a direct pathway in the EAM is required in order to replicate the EAM in a 3D format. The OCT method of reconstructing a 3D image of the EAM has limitations along with the infrared light technology. Infrared light technology works best only when conditions are met such as a direct line of site. At any time if the probes' infrared light position is misaligned, it will be unable to reconstruct the image of the ear as the pathway is not within line of sight. Also, the EAM varies from patient to patient where often times the EAM bends are not within line of site. OCT method of the reconstruction process requires good positioning of the probe head where the light source is emitted. Thus, this approach is not effective at passing second or third bends, if existing, in the EAM as a direct path is not obtainable. Additionally, the 3D images itself will require some manipulation in order extract the relevant shape of the EAM from the images. Cepholometric radiographic imaging is limited in this way as well. Also, if any cerumen or foreign object is within the pathway of the EAM, the OCT method of scanning would be unable to capture the EAM beyond this point.

Existing methods of replicating the pinna and or EAM requires some form of object implanted in the ear in order to achieve replicating for prosthetic development for the treatment of disorders or protection of the human auditory system. Accordingly, there is a need for a less invasive, less time consuming, yet accurate method of producing auditory canal implants that is not delayed by the presence of matter within the auditory canal.

SUMMARY OF THE INVENTION

In accordance with an aspect of the present invention, there is provided a method performed by at least one computing device, the method comprising: extracting measurements of at least one auditory canal from at least one computerized imaging scan of the at least one auditory canal devoid of physical measurement aids; determining eligibility for at least one auditory canal device at least partly by comparing the measurements of the at least one auditory canal with predetermined measurements of the at least one auditory canal device; and providing an indication of the eligibility determination contemporaneously with the measurement extracting.

In accordance with an aspect of the present invention, there is provided a system comprising at least one computer processor coupled to a non-transitory computer-readable medium or media comprising computer-executable instructions configured to cause the at least one computer processor to: extract measurements of at least one auditory canal from at least one computerized imaging scan of the at least one auditory canal devoid of physical measurement aids; determine eligibility for at least one auditory canal device at least partly by comparing the measurements of the at least one auditory canal with predetermined measurements of the at least one auditory canal device; and provide an indication of the eligibility determination contemporaneously with the measurement extracting.

In accordance with an aspect of the present invention, there is provided a method performed by at least one computing device, the method comprising: scanning at least one facial contour of a person at least partly by using at least one computer tomography ("CT") scanner coupled to the at least one computing device; extracting measurements of the at least one facial contour from at least one computerized imaging scan of the at least one facial contour produced by the at least one CT scanner; determining acceptability of the extracted measurements for production of at least one prosthetic based at least partly on predetermined requirements of the at least one prosthetic; and providing an indication of the acceptability determination contemporaneously with the measurement extracting and the scanning.

In accordance with an aspect of the present invention, there is provided a system comprising at least one computer processor coupled to a non-transitory computer-readable medium or media comprising computer-executable instructions configured to cause the at least one computer processor to: scan at least one facial contour of a person at least partly by using at least one computer tomography ("CT") scanner coupled to the at least one computing device; extract measurements of the at least one facial contour from at least one computerized imaging scan of the at least one facial contour produced by the at least one CT scanner; determine acceptability of the extracted measurements for production of at least one prosthetic based at least partly on predetermined requirements of the at least one prosthetic; and provide an indication of the acceptability determination contemporaneously with the measurement extracting and the scanning.

Various other embodiments are described.

In this respect, before explaining at least one embodiment of the invention in detail, it is to be understood that the invention is not limited in its application to the details of construction and to the arrangements of the components set forth in the following description or the examples provided therein, or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

Figure 1:
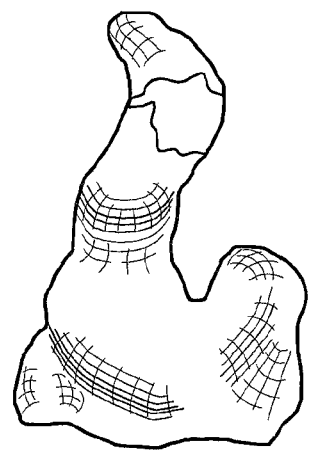
FIG. 1 illustrates a rendering of an auditory canal resulting from a traditional impression method.
Figure 2:
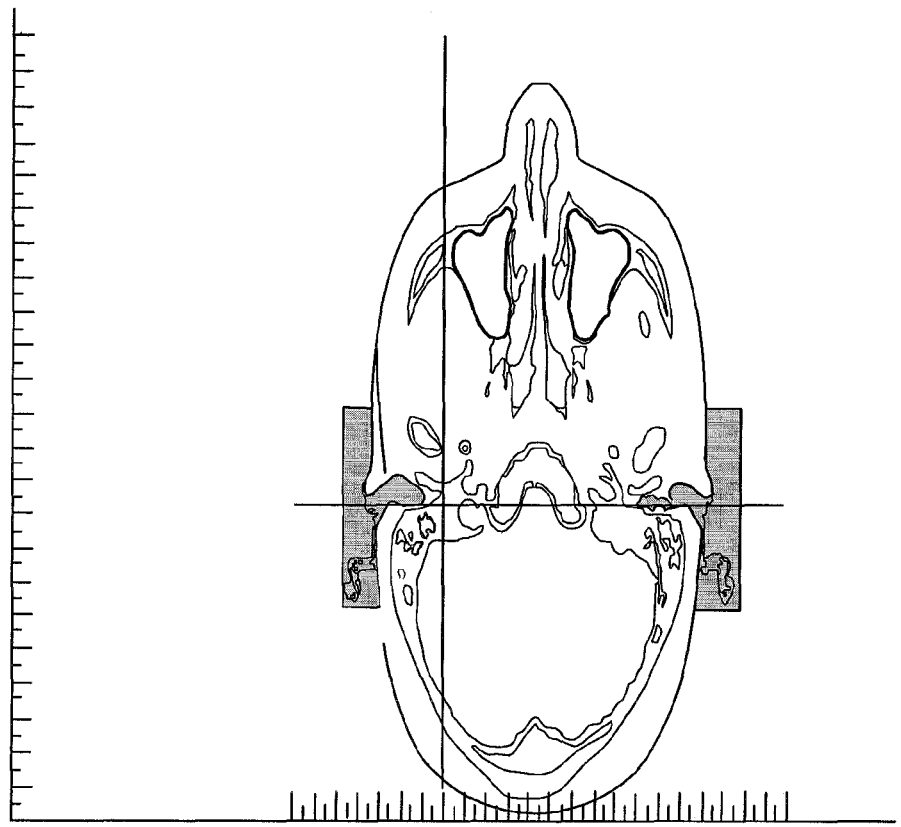
FIGS. 2 to 8 are exemplary views of images produced in accordance with aspects of the present invention.
Figure 3:
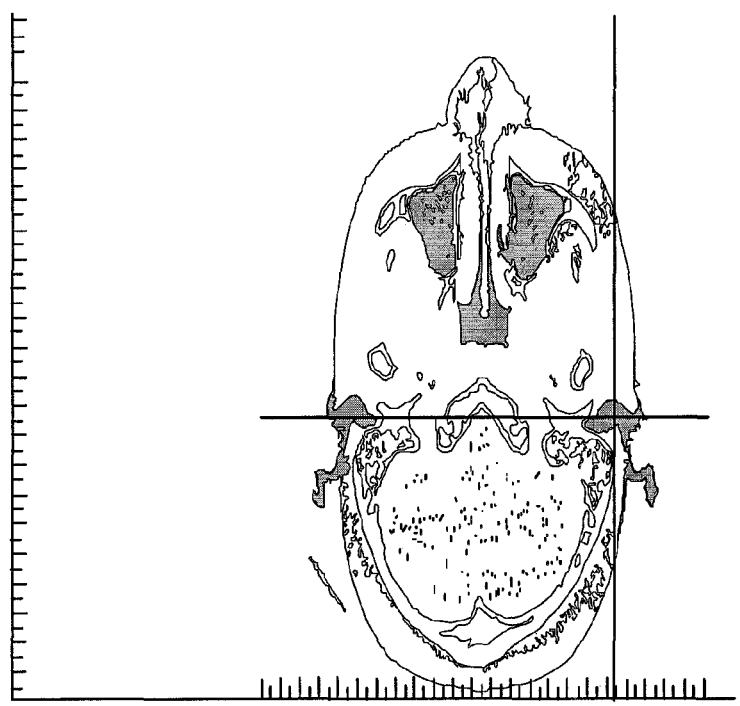
Figure 4:
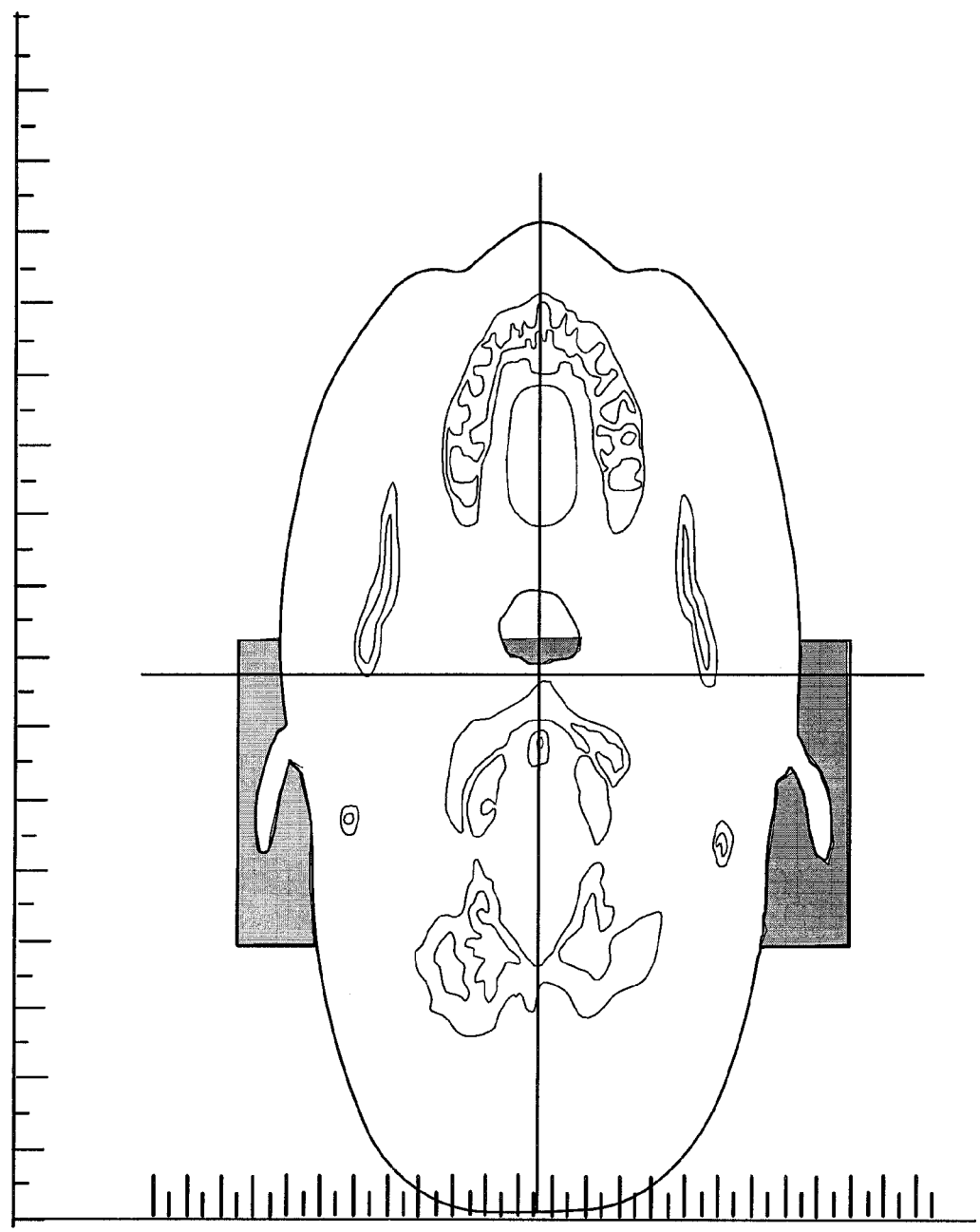
Figure 5:
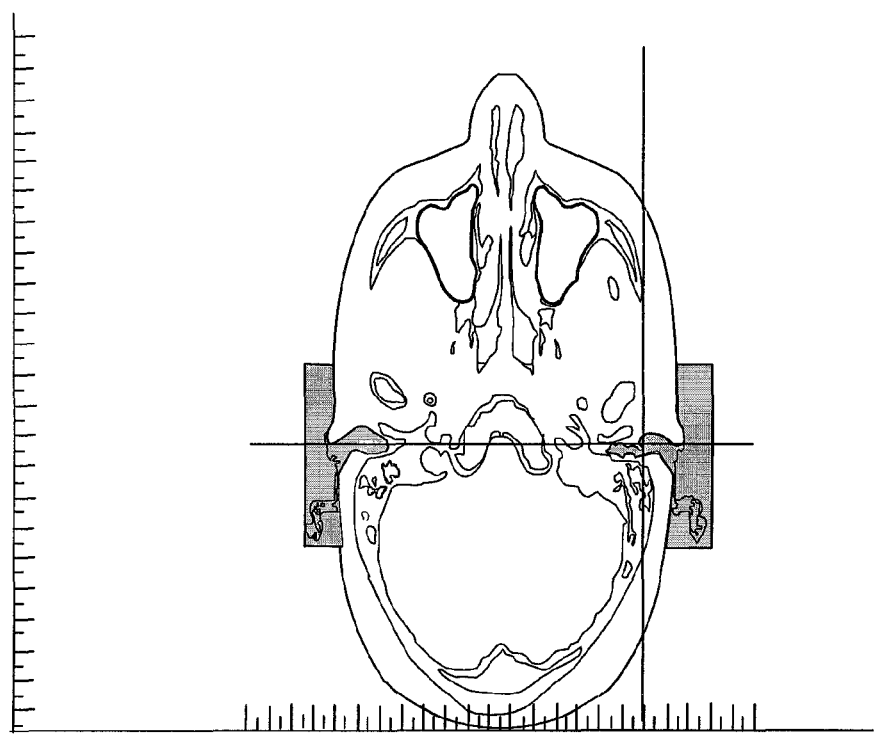
Figure 6:
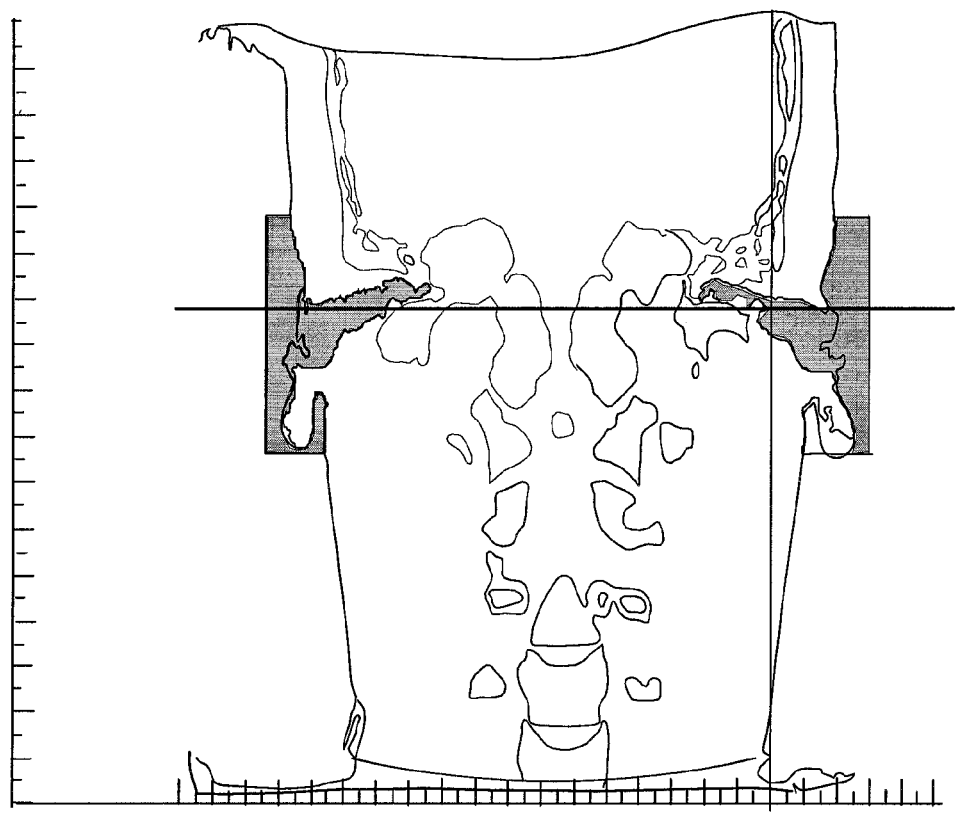

The present invention provides a method and system for measuring the shape of a patient's auditory canal without inserting any material in the auditory canal, optionally without contacting the patient at all, optionally by contacting the patient less than using prior art methods.

In an aspect of the invention, a method is provided, performed by at least one computing device, or system, the method comprising: extracting measurements of at least one auditory canal from at least one computerized imaging scan of the at least one auditory canal devoid of physical measurement aids; determining eligibility for at least one auditory canal device at least partly by comparing the measurements of the at least one auditory canal with predetermined measurements of the at least one auditory canal device; and providing an indication of the eligibility determination contemporaneously with the measurement extracting. Measurement aids commonly used in determining measurements of a patient's auditory canal (ear canal) include auditory canal impression materials and radiographic markers. By using such measurement aids, prior art techniques either necessitate using new impression materials each time a measurement is required, or if the first impression materials are misplaced or damaged, or require inserting physical materials deep into the patient's auditory canal, which may be uncomfortable or painful for the patient. Instead, the method of the present invention employs a computed tomography ("CT") scanner to scan the patient's auditory canal without contacting the patient and without inserting any material into the patient's auditory canal. The resulting computerized imaging scan, or scan, may be analyzed by the at least one computing device to extract measurements of the auditory canal. Once the measurements are extracted, the at least one computing device may compare the measurements to known measurements of one or more auditory canal devices, such as hearing aids, to determine whether a particular auditory canal device is suitable for the measured auditory canal. An auditory canal device having measurements that exceed the measurements of the auditory canal extracted from the scan would not be eligible for insertion or implantation into the auditory canal. However, an auditory canal device that is approximately the same size or smaller than the auditory canal may be eligible. Optionally, depending on requirements of a particular auditory canal device, known to the at least one computing device, it may also be necessary that an auditory canal device be not smaller than the auditory canal by a particular predefined threshold. The CT scanner may orbit the patient's head in a predefined or customized path, and may scan one or both of the patient's ears and auditory canals in the same or subsequent scans. The at least one computing device is required in order to either control the CT scanner, or to receive the scan(s) produced by the scanner, extract the measurements therefrom, and perform the eligibility determination as described herein. By using at least one computer in this way, the eligibility determination may be performed substantially contemporaneously with the measurement extracting. The eligibility determination may also be performed substantially contemporaneously with the scanning the auditory canal(s). In this way, if the computing device indicates that additional scanning or measurement extracting is necessary after performing the eligibility determination, the additional steps may be performed without requiring the patient to return for another appointment. In prior art methods, where an ear mold impression is made, the impression is typically either analyzed later or shipped off-site for analysis in order to fit a suitable auditory canal device, while the patient is sent home. Accordingly, in prior art methods it is not typically known until sometime later whether or not the ear mold must be re-made for any one of a variety of reasons. In the present method, the at least one computing device may make a determination regarding whether further measurements are required relatively quickly while the patient remains by the scanner. The patient may therefore be saved from having to return for more measurements, and may receive the patient's auditory canal device more quickly than in prior art methods.

Physical measurement aids that are typically used in prior art methods, but not used in the method of the present invention include at least auditory canal impression materials and radiographic markers during the scanning.

Each auditory canal of the patient generally comprises a tympanic membrane within the auditory canal. The auditory canal includes a first bend and a second bend, the second bend being between the first bend and the tympanic membrane. While the scanner may obtain a scan of each of these elements of the auditory canal, and more, in accordance with an aspect of the present invention, the extracted measurements of the at least one auditory canal comprise measurements of the at least one auditory canal between the second bend and the tympanic membrane. Measurements of this area are important for determining eligibility of an auditory canal device for use in the respective auditory canal.

A type of scanner that may be used to scan the patient's auditory canal(s) includes a cone beam computed tomography ("CBCT") scanner. Optionally, the scanner may orbit the patient's head in a predefined path. In the event that additional measurements are required, or if the patient's head or auditory canals are unusual, either in shape, or density, or for other reasons, a customized orbital path may be created in order to create the computerized imaging scan(s).

In an aspect of the invention, a method is provided integrating two dimensional ("2D") images from spiral computed tomography and cone beam computed tomography to create a three dimensional ("3D") digital image of a pinna and external auditory meatus ("EAM"). The 3D image may be known as a digimold, or digital mold, image. The method produces a 3D digimold image replication of the pinna and EAM allowing integration and prosthetic creation in the treatment of human auditory disorder (hearing loss). In particular, the digimold method is the process of developing a digital impression of the pinna and EAM without implantation of any object or the use of any impression material in the EAM. The digimold image may be obtained even where cerumen is present in the auditory canal, or where the patient has an ear infection. In advantage of the method of the present invention includes not having to wait for pre-existing conditions in the auditory canal to be treated prior to measuring the auditory canal because the imaging technique employed in the present invention does not require contact with the patient, and in particular does not require any material to be inserted into the patient's auditory canal. The method of the present invention also may prevent the patient from having an allergic reaction as there is no direct contact with human epidermis.

No specific patient positioning toot or aid may be required to scan the patient. As long as the areas of interest (e.g. ear drum, ear canal and external ear) are captured in the volume of the CT or CBCT, then no specific angle or patient head position is required. However, the if the measurements obtained from scans produced by the scanner are not acceptable, additional scans are alternate scanning angles or scanning distances may be performed. The data may be acquired as a 3D volume and the separation of the area of interest may be based on radiographic density of tissues.

One consideration may include, since the present invention method largely follows air patency, if there is a large amount of ear wax obstructing the ear canal then removal of ear wax may be sometimes required. However, this is not necessarily required since the radiopacity of ear wax is still different from that the of skin of the ear canal, and thus measurements of the auditory canal may still be determined even in the presence of ear wax. Another consideration may be that if there is a portion of the external ear or the transition between the ear canal and the external ear that is deformed temporarily due to a heavy ear ring or headphone or hearing aid present, this may be removed prior to imaging. Another consideration may be that any foreign metallic object in the region of the ear canal (e.g. ear ring) may need to be removed as the x-rays hitting this metallic object can produce scatter distortion of the 3D image. During the imaging no part of the machine should touch the patient's external ear or ear canal and, optionally, the patient should have the patient's mouth comfortably closed.

FIG. 1 shows an image of an EAM resulting from a traditional impression method. An oto-block can be seen in pale shading, while the darker shading is the impression material. In this example, the impression material was able to bypass the oto-block. This result would not occur if the method of the present invention was used, as no material is inserted into the auditory canal.

It may be an advantage of the present invention that a patient may be treated for cerumen or ear infections while a custom hearing aid device is being developed based on measurements taken of the patient's auditory canal. Treatment of cerumen may require one or more referrals to a specialist, who may be booked for months into the future. Not having to wait to see the specialist may significantly reduce the time to treat the patient's hearing loss or auditory disorder. Where the patient is a child, treatment of the child's auditory disorder may be achievable more quickly than using traditional impression techniques, resulting in cognitive auditory treatment earlier during critical stages of the child's brain development.

The method of the present invention may begin by performing a spiral CT or a CBCT scan of the patient's auditory canal. During the scan, multiple images may be created representing different views or slices of the auditory canal. Any images or image data produced by each scan may be exported into a universal file format called a Digital Imaging and Communications in Medicine ("DICOM") file. DICOM is a standard for handling, storing, printing, and transmitting information in medical imaging. The DICOM standard includes a file format definition and a network communications protocol. The communication protocol is an application protocol that uses a standard such as TCP/IP to communicate between systems. DICOM files can be exchanged between computer devices, such as client computers and server computers, that are capable of receiving image and patient data in DICOM format. DICOM is acceptable as a standard form for handling, storing, printing, and transmitting information of medical imaging for members of the National Electrical Manufactures Association (NEMA).

In order to create a 3D image of the auditory canal, the scanned image data may be segmented by the scanner or the at least one computing device. The segmentation process partitions the scanned image data image into multiple segments in order to locate common elements of the auditory canal shown in the image data, such as auditory canal boundaries. Once segmented, multiple 2D images from the DICOM file may be mapped to a 3D co-ordinate system. If necessary, 3D data points between the 2D image segments may be interpolated using one of a variety of interpolation algorithms. The resulting 3D image can be rendered and areas of anatomic interest may be selectively rendered and viewed. The 3D image may also be printed using 3D printing techniques using a standard stereo lithography ("STL") file.

Accordingly, the at least one computing device may partition the at least one computerized imaging scan into a plurality of image segments. The at least one computing device may locate common elements of the auditory canal shown in the plurality of image segments, and may map the plurality of image segments to a 3D co-ordinate system based at least partly on the located common elements. The mapped plurality of image segments may then be rendered as at least one 3D image. The locating common elements may comprise identifying at least one common element based at least partly on patient skin density data captured in the at least one computerized imaging scan. The at least one computing device may also identify common elements in the 3D image located beyond the tympanic membrane in the at least one auditory canal and remove the identified common elements from the 3D image, as these common elements may not be necessary in determining eligibility for an auditory canal device.

A portion of the ear canal that is imaged may be selected that is of interest in the fabrication of the hearing aid. The information captured generally follows the flow of air and thus captures all detail that is external to the tympanic membrane (ear drum), continuous with the external auditory canal and continuous with the external ear (pinna). It is also possible, depending on patency of the sinuses in the mastoid region, that the mastoid air sinuses can be captured in the scan segmentation process. The area of interest will depend on the depth of the prosthetic attempted and the amount of external show that is involved. It is unlikely that the mastoid air cells would be of any interest and thus the at least one computing device may be configured to delete this area (for example, in 3D).

Either the 2D images or the 3D image may be communicated through a communications network to a manufacturer, vendor, or other entity for the creation, development, or modification of prosthetics or related custom products. Custom products that may be created, developed, or modified by using data provided in the communicated image(s) may include hearing aids, ear molds for hearing aids, headphones, swim plugs, and any products required for specific fitting within the patient's EAM. As the DICOM file(s) may be transmitted between parties, there may be no need to ship any material between clinician and auditory canal device manufacturer. The measurements may be formatted into a data file in accordance with a standardized computerized file format, such as DICOM. The data file may be transmitted, optionally together with an identification of at least one auditory canal device to at least one computer server over a communications network for analysis. The eligibility determination may therefore be based at least partly on a determination of eligibility received from the at least one computer server.

Accordingly, the at least one computing device may transmit the measurements (either the measurements themselves or the computerized imaging scan(s) from where the measurements may be extracted) and an identification of the at least one auditory canal device to at least one computer server over a communications network. The at least one computing device may then receive data from the computer server over the communications network, the data including a determination of the extracted measurement acceptability for use in the determining eligibility. The at least one computing device may then provide an indication of whether additional scanning is required in accordance with the extracted measurement acceptability determination. Any indications provided by the at least one computing device may be auditory signals, or may be displayed on a display device of the at least one computing device or a separate display device in communication with the at least one computing device. The indication may also comprise a printout from a printer device of or in communication with the at least one computing device. If the extracted measurements are deemed to be not acceptable for use in fitting an auditory canal device, the at least one computing device may control the scanner to obtain one or more additional, or replacement, scans.

In an implementation, manufacturers may be able to produce the custom fitted prosthetics from images sent directly from the scanning device or at least one computing device. The raw image could be customized to a manufacturer's specification and loaded towards the manufacturer's own optical coherence tomography ("OCT") scan.

Optionally, an implementation of the method of the present invention may produce scans of both of a patient's ears in approximately 30 seconds or less. Transmitting the image data through DICOM standard communication to an auditory canal device manufacturer may occur immediately thereafter. As an unlimited number of copies of the DICOM files may be made and transmitted, should the manufacturer misplace the DICOM files it receives, the clinician may simply resend the DICOM files to the manufacturer. This compares favourably with traditional impression techniques where another impression must be made requiring another patient visit should the initial impression be lost.

Optionally, according to another aspect of the present invention, a clinician may perform an otoscopic examination of the patient prior to any scanning in order to determine if a digimold image could be successfully produced. During the otoscopic examination, the clinician is required to have some knowledge of the anatomy of the patient's pinna and EAM to ensure that the method of the present invention could accurately obtain a representation of the anatomy for the development of a prosthesis.

Since custom hearing aids are designed and fitted for individual patients, the at least one computing device may analyze measurements extracted from the computerized imaging scans collected from the method of the present invention and recommend suitable custom hearing aids for the patient based at least partly on measurement data of the patient's auditory canal(s) and measurement data of one or more auditory canal devices known to the at least one computing device. Before offering a hearing aid as a treatment option, factors including age of the patient, EAM types and prosthesis requested may also be considered. The age of the patient may be a concern where the patient is a child, and in particular, a young child. The child may be required to sit still for the duration of the scanning, typically about 30 seconds. If the child is unable to remain still during the scan, the obtained image should be analyzed to cross reference the accuracy of the image with the patient's ear anatomy viewed during otoscopic examination.

Each patient's EAM is different. Some auditory canals may have bends that are so narrow that the entire pathway towards the tympanic membrane is not visible through otoscopic examination. In such cases, tympanometry may be performed prior to scanning the patient's auditory canal. Tympanometry provides information of the movement of the tympanic membrane, which provides information of the EAM pathway as well. Once the pathway of the EAM towards the tympanic membrane is verified safe, then the scanning and hearing aid fitting process may continue.

Although the method of the present invention is primarily useful for the production of custom fitted in-ear devices, the method of the present invention may also be used in the production of off-the-shelf prosthesis devices.

In accordance with an aspect of the present invention, a 3D image may be produced by differentiating regions by a threshold value, such as density of the image. For example, the density of the air space within the pinna and EAM may differ from the density of the skin of the pinna and the EAM. Accordingly, the threshold value may determine the shape and dimensions of the desired anatomy of the patient's entire head. To be specific, the pinna and the EAM may be captured alone or, if desired, together with information of the tympanic membrane and beyond. The method of the present invention may produce a digimold image, or virtual impression, that includes a flood fill of the entire area of the patient that is in contact with the ear canal (everything outside of the head), thereby creating a simultaneous impression of the face, nose, and airway.

The digimold image may then be cropped by focusing only on the area of interest such as the pinna and EAM of both sides of the patient's head. Alternatively, only the pinna and EAM may be captured in the digimold image in the first place so that less cropping may be necessary. Further information captured beyond the tympanic membrane may also be removed from the captured image, by segmenting, or slicing the 3D image in order to focus predominantly on the pinna and EAM. A final decision is then required as to the quality of the final 3D object created from the data. This involves selection of the resolution and the grey value or contour value.

In an implementation of the present invention, the CBCT scanner may scan the patient's auditory canal by orbiting the patient's head in a predefined or customized path.

Figure 7:
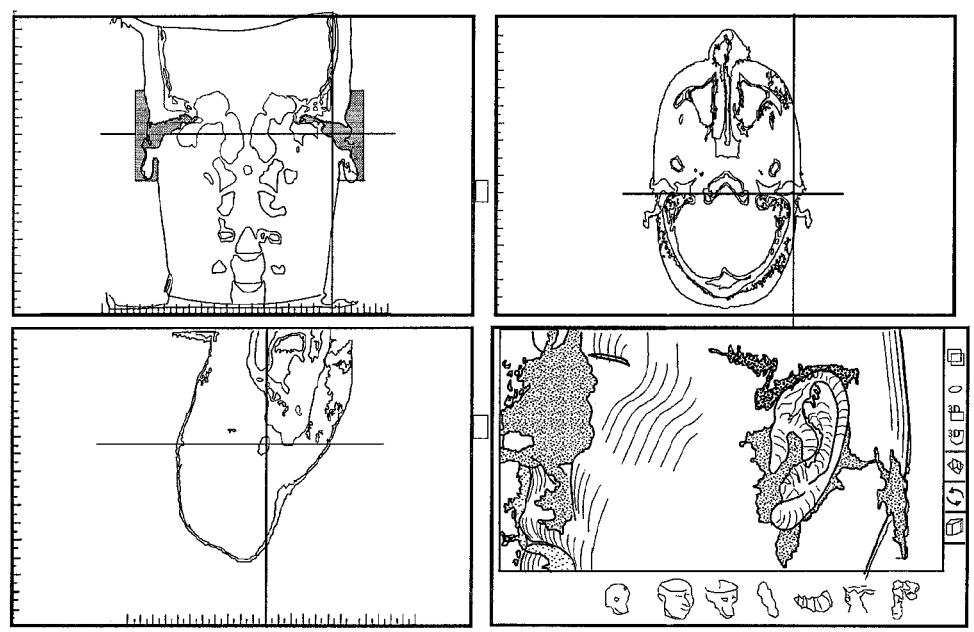
Figure 8:
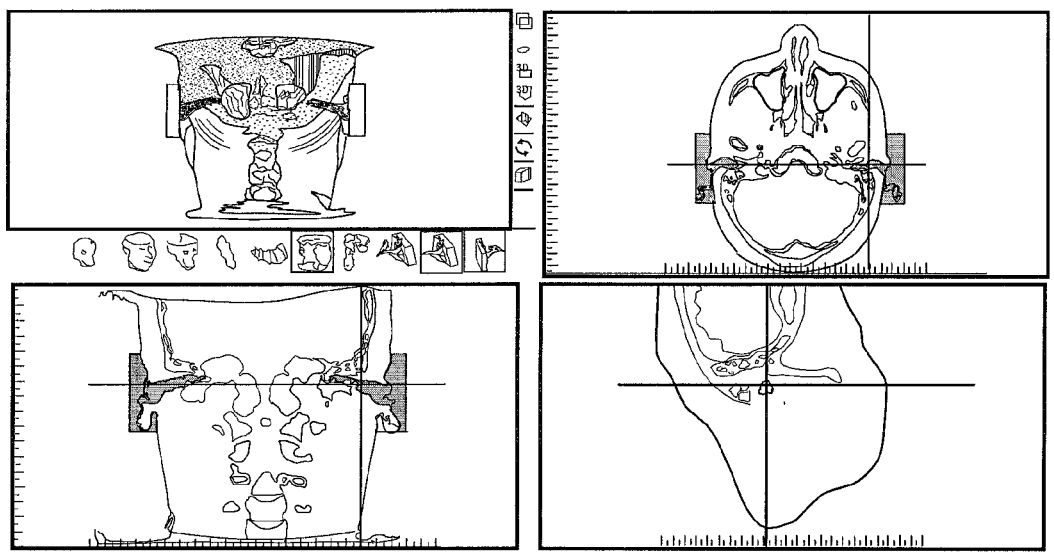

FIGS. 2 to 6 are exemplary views of images produced in accordance with an aspect of the present invention. The images may be further processed prior to communication to the manufacturer of an in-ear device for the patient. Optionally, each image could be isolated into an image of one or both ears. FIGS. 7 and 8 show multiple exemplary views of images produced in accordance with an aspect of the present invention.

In an implementation of the present invention, the patient may be seated still and the CBCT machine orbits around the patient's head in order to provide the option of capturing both ears either simultaneously or separately. Acquisition time, the duration of time where the CBCT is actively scanning the patient, and scan resolution may vary from machine to machine. One machine, known as PaxFlex 3D may capture images with dimensions of 8 mm×5 mm with an acquisition time of 24 seconds. This machine has an exposure time of about 8.9 seconds at a resolution of 0.3 mm and is capable of a resolution of 0.125 mm with an exposure time of about 26.9 seconds. With most CBCT machines, the time required is generally less than 30 seconds, which is less than the traditional EAM impression method that requires several minutes depending on the density of the patient's pinna and or EAM and the shore of the impression materials.

Figure 9:
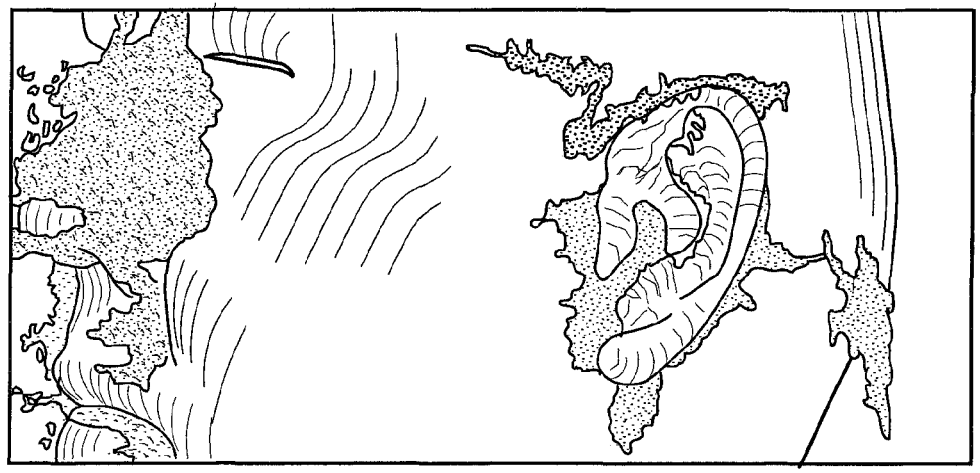
FIG. 9 shows an initial image of an entire patient head scanned using a CBCT machine in accordance with an aspect of the present invention.
Figure 10:
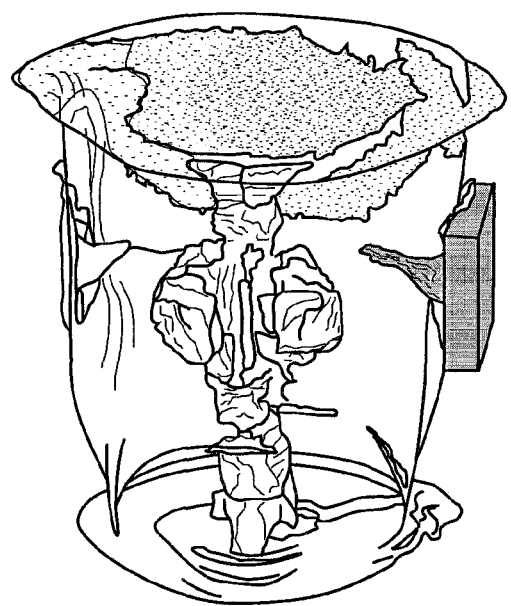
FIG. 10 shows an image during the process of segmentation of the patient's right ear canal and external ear cavities in order to isolate the EAM in accordance with an aspect of the present invention.
Figure 11:
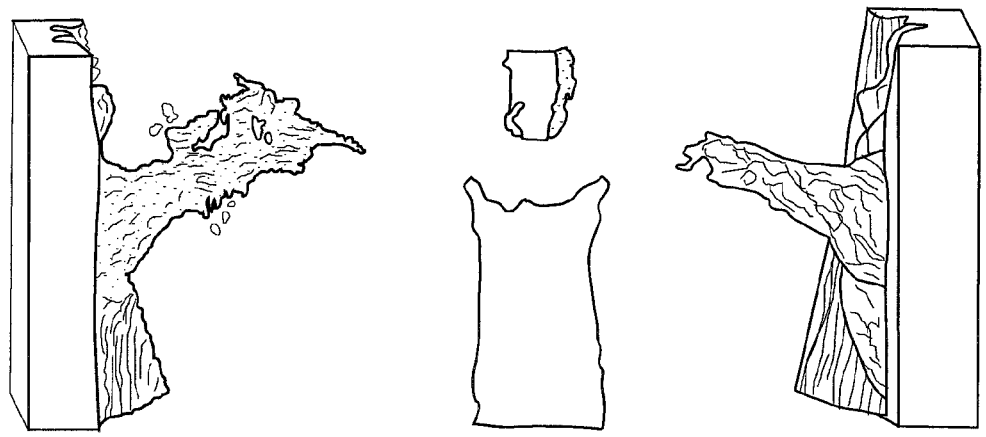
FIG. 11 shows an image of the patient's right and left ear EAM in accordance with an aspect of the present invention.
Figure 12:
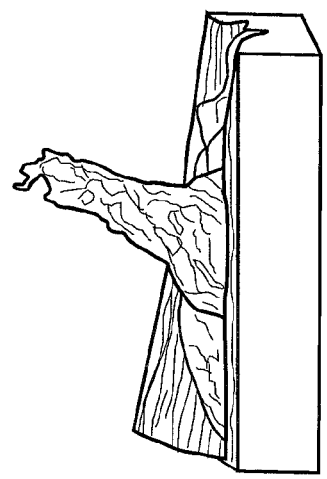
FIG. 12 shows an image indicating only unilateral impression of the patient's left ear EAM when only one side is required, in accordance with an aspect of the present invention.
Figure 13:
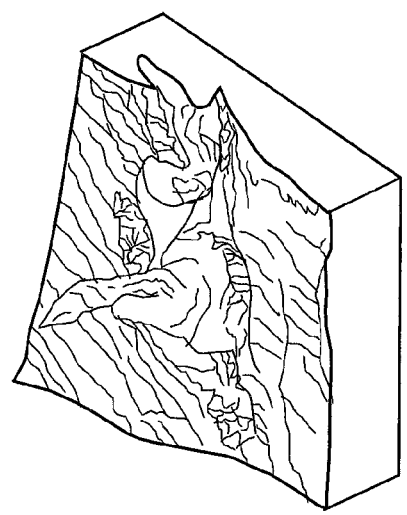
FIGS. 13-15 show different perspective views of the segmentation achieved of the patient's left ear EAM shown in FIG. 12.
Figure 14:
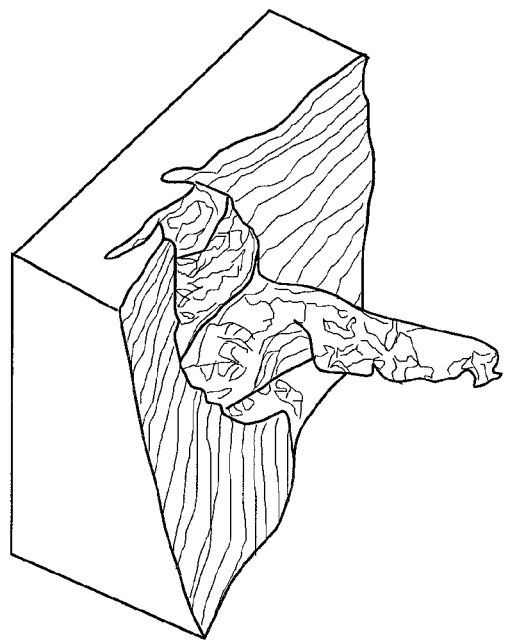
Figure 15:
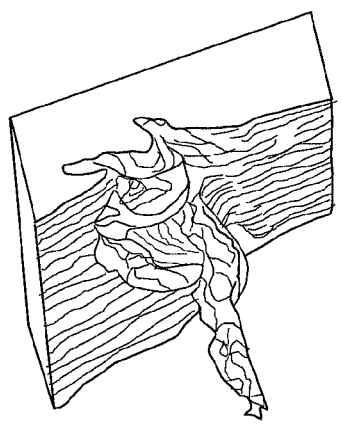
Figure 16:
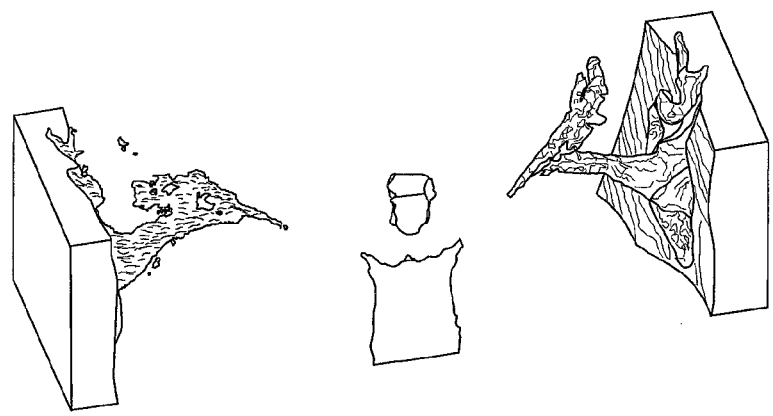
FIG. 16 shows images of both ears viewed simultaneously, in accordance with an aspect of the present invention.
Figure 17:
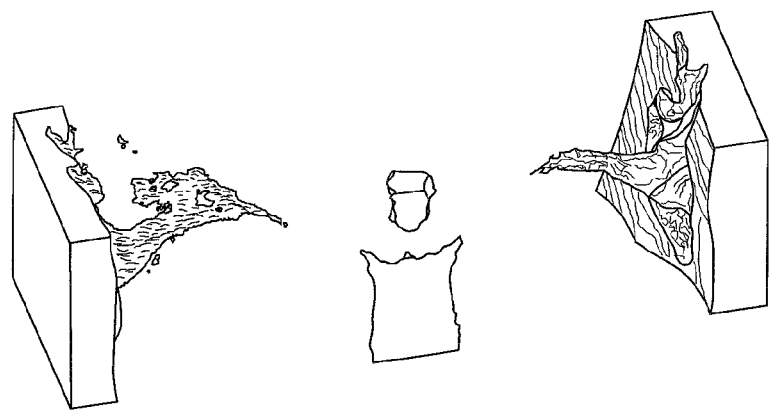
FIG. 17 shows the same view as FIG. 16 with a segmented view of the patient's left ear EAM such that colour coordination may also be achieved in the image views where red coloured segments indicate the patient's right ear and blue coloured segments indicate the patient's left ear.
Figure 18:
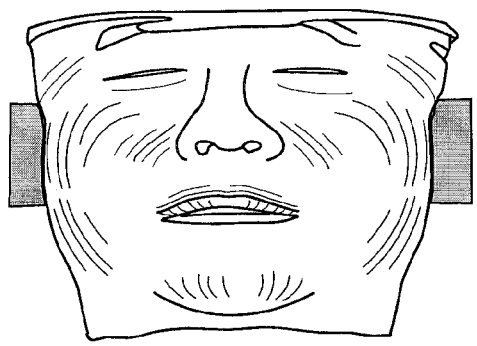
FIGS. 18-20 show different exemplary views of the patient's head with varied shading and segmentation to show the context of the auditory canal within the context of the patient's head, in accordance with aspects of the present invention.
Figure 19:
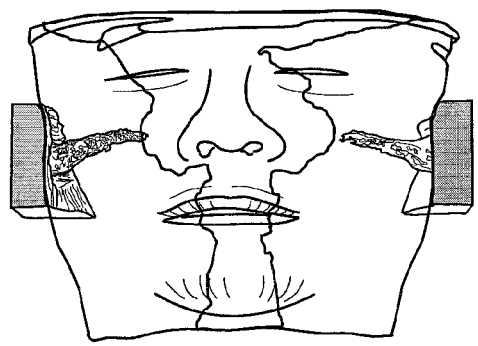
Figure 20:
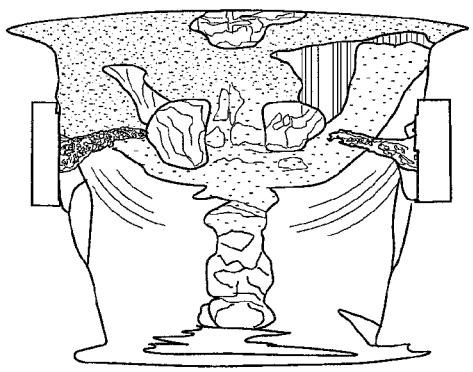
Figure 21:
FIGS. 21-22 show varied views of both right and left ear canals of a patient in accordance with aspects of the present invention.
Figure 22:
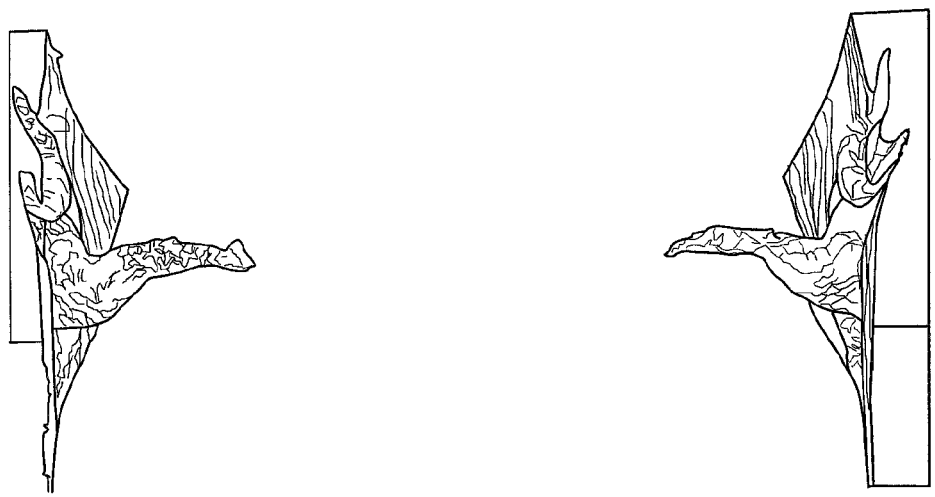
Figure 23:
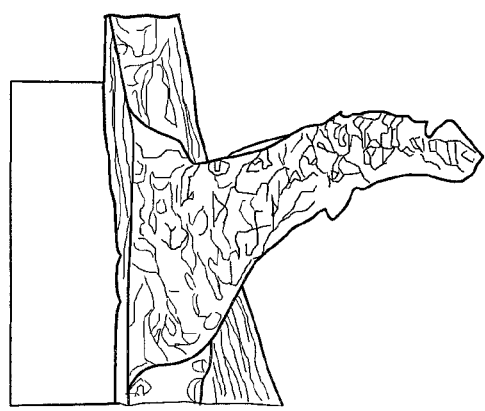
FIGS. 23-27 show varied views of the right ear canal in accordance with aspects of the present invention.
Figure 24:
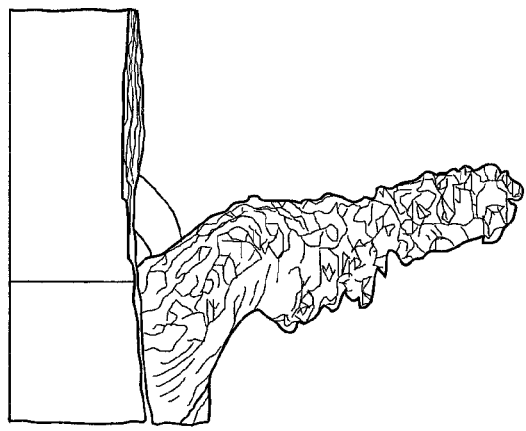
Figure 25:
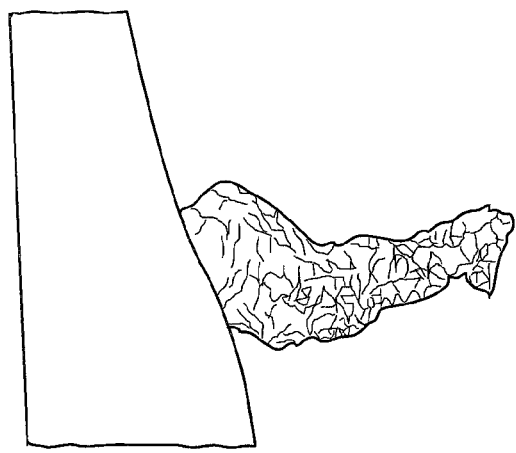
Figure 26:
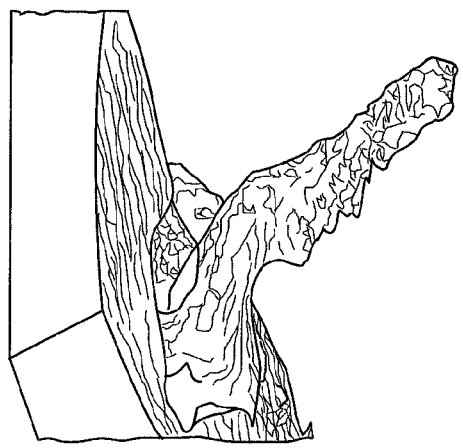
Figure 27:
Figure 28:
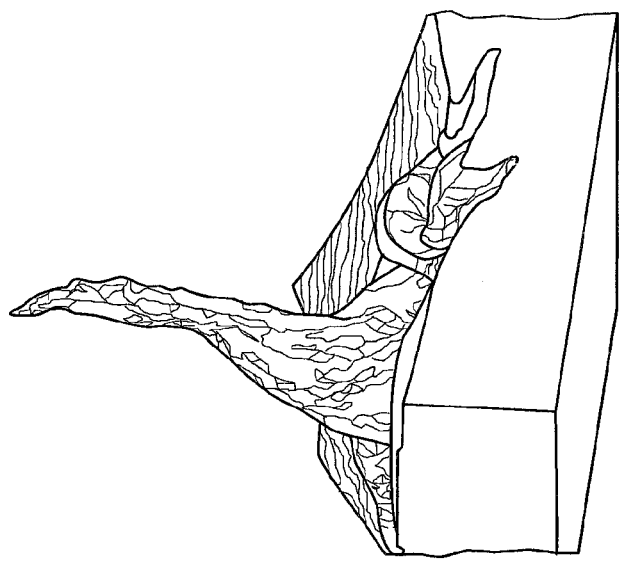
FIGS. 28-30 show varied views of the left ear canal in accordance with aspects of the present invention.
Figure 29:
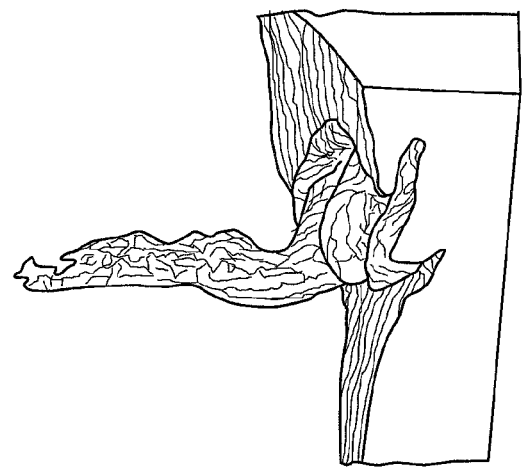
Figure 30:
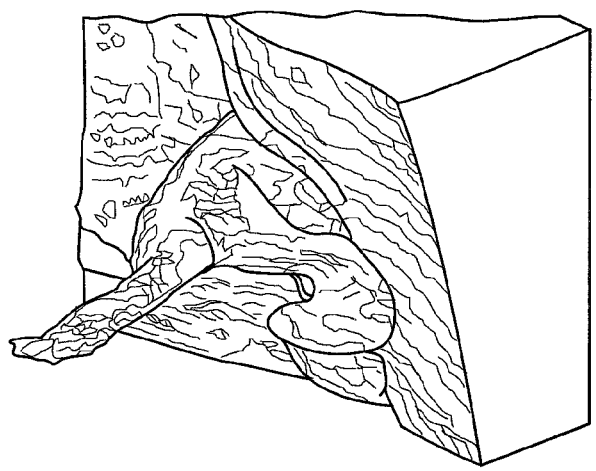
Figure 31:
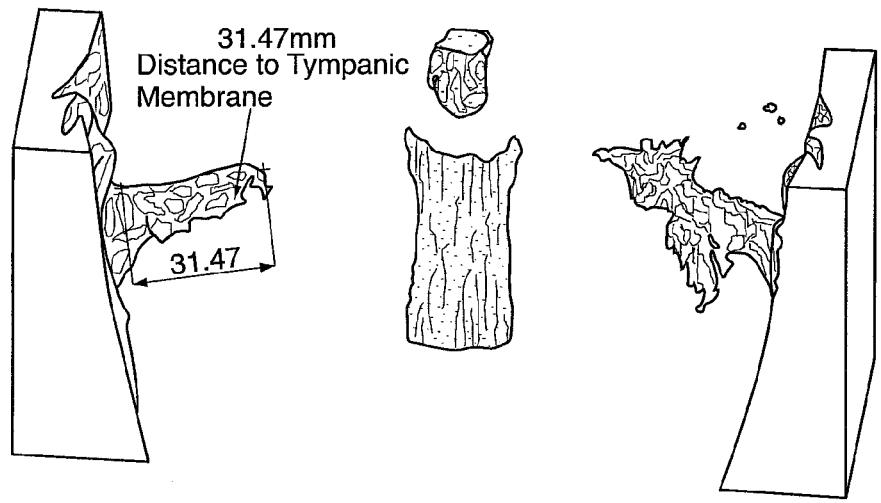
FIGS. 31-32 show scanned images with measurements indicated thereupon in accordance with aspects of the present invention.
Figure 32:
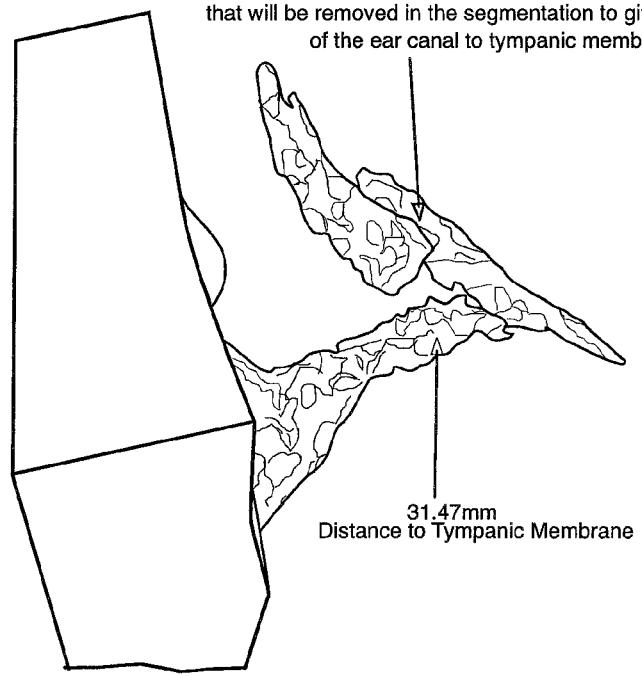

The following figures are exemplary views of images produced in accordance with aspects of the present invention: FIG. 9 shows an initial image of an entire patient head scanned using a CBCT machine; FIG. 10 shows an image during the process of segmentation of the patient's right ear canal and external ear cavities in order to isolate the EAM; FIG. 11 shows an image of the patient's right and left ear EAM; FIG. 12 shows an image indicating only unilateral impression of the patient's left ear EAM when only one side is required; FIGS. 13-15 show different perspective views of the segmentation achieved of the patient's left ear EAM shown in FIG. 12; FIG. 16 shows images of both ears viewed simultaneously. FIG. 17 shows the same view as FIG. 16 with a segmented view of the patient's left ear EAM such that colour coordination may also be achieved in the image views where red coloured segments indicate the patient's right ear and blue coloured segments indicate the patient's left ear; FIGS. 18-20 show different exemplary views of the patient's head with varied shading and segmentation to show the context of the auditory canal within the context of the patient's head; FIGS. 21-22 show varied views of both right and left ear canals of a patient; FIGS. 23-27 show varied views of the right ear canal; FIGS. 28-30 show varied views of the left ear canal; and FIGS. 31-32 show scanned images with measurements indicated thereupon.

Most hearing aids are shaped to reach approximately the second bend of the EAM. Some recently developed hearing aids utilize deeper ear canal custom products that pass the second bend in the EAM. Precise measurement of the depth of the tympanic membrane is critical for the use of the deeper ear canal products as inaccurate measurements may cause damage to the tympanic membrane. Manufacturers of such hearing aids such as Phonak Lyric, Starkey Laboratories, and others.

Figure 33:
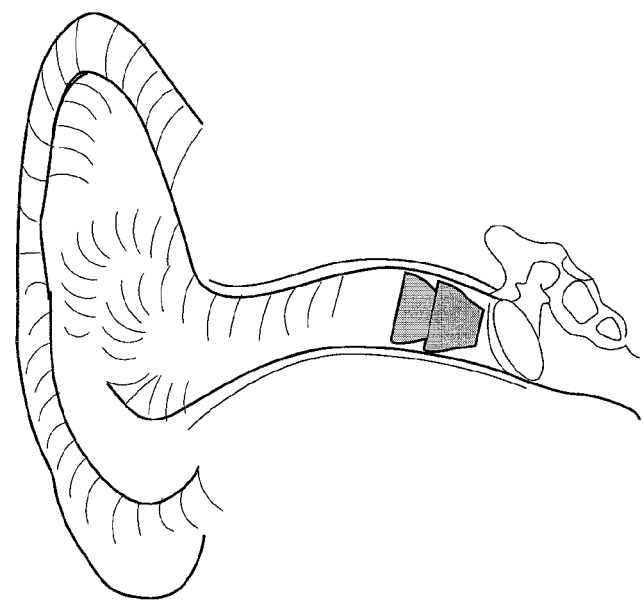
FIG. 33 shows a representation of a Phonak Lyric hearing aid inserted into a patient's auditory canal.
Figure 34:
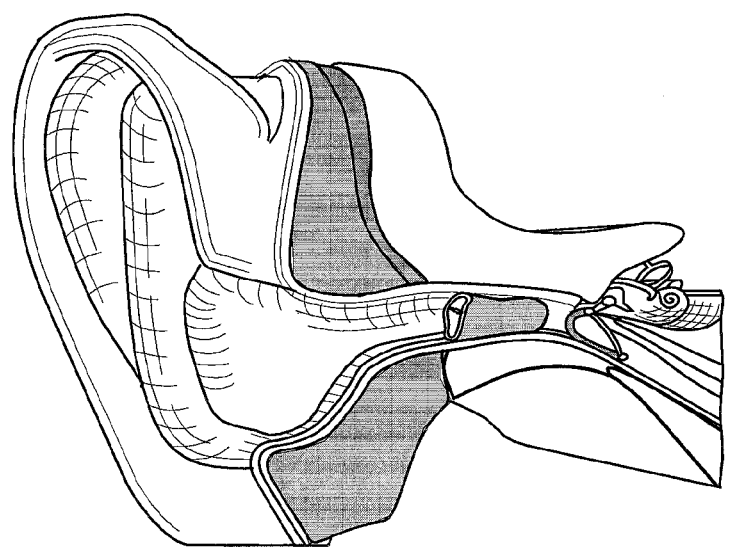
FIG. 34 shows a representation of a Starkey Laboratories hearing aid showing the device positioned millimeters away from the tympanic membrane in the EAM.
Figure 35:
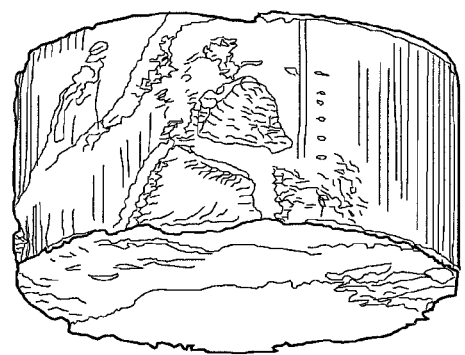
FIGS. 35-43 are exemplary views of images produced in accordance with aspects of the present invention showing image sizing with segmentation processing.
Figure 36:
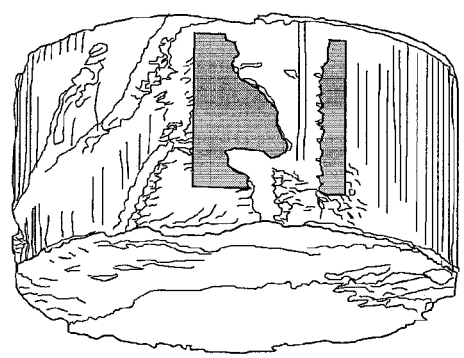
Figure 37:
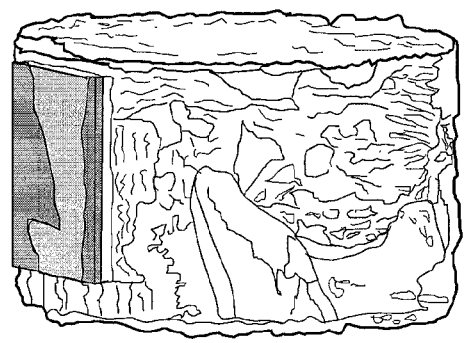
Figure 38:
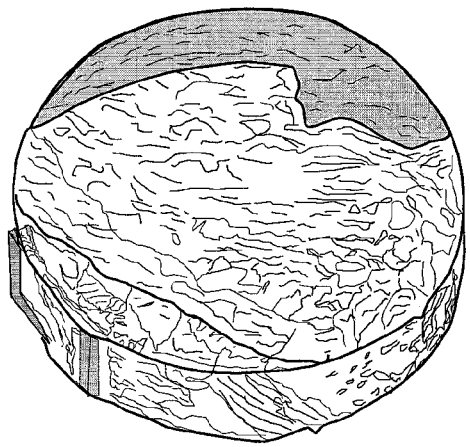
Figure 39:
Figure 40:
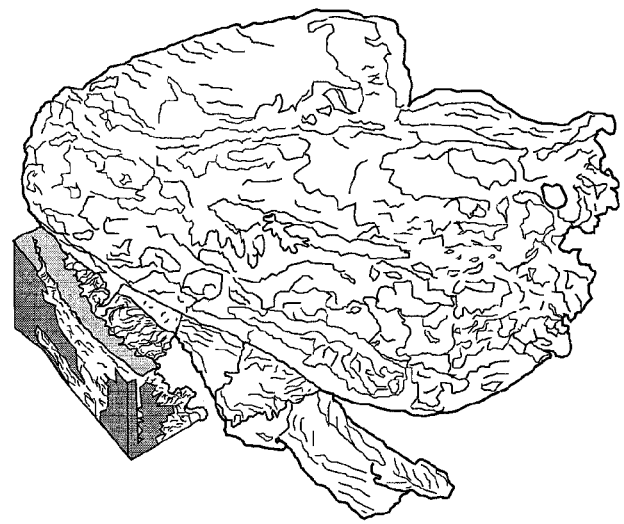
Figure 41:
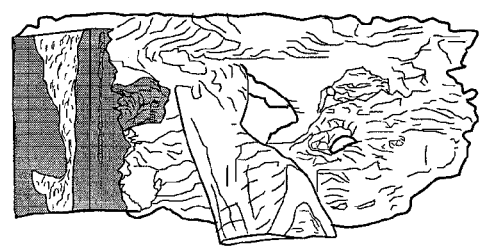
Figure 42:
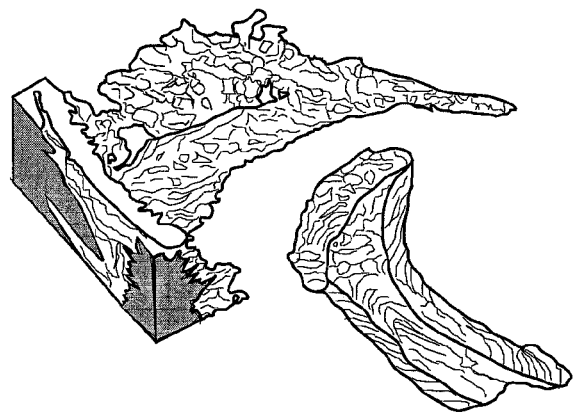
Figure 43:
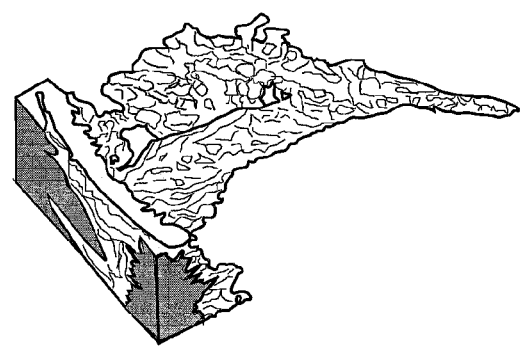

FIG. 33 shows a representation of a Phonak Lyric hearing aid inserted into a patient's auditory canal. The Phonak Lyric is designed to be placed 4 mm from the tympanic membrane and requires that the patient's EAM be within certain dimensions. FIG. 34 shows a representation of an invisible-in-the-canal ("IIC") device from Starkey Laboratories showing the device positioned millimeters away from the tympanic membrane in the EAM. An ear impression that extends 10-12 mm beyond the second bend in the EAM may be required for an accurate and comfortable fit of an IIC device. In an implementation of the method of the present invention, the auditory canal past the second bend may be measured without inserting any material in the patient. Furthermore, since the DICOM image file may be transmitted to the manufacturer from a computer system accessible to the clinician, Phonak in this case, optionally including a request for a specific model of hearing aid, the manufacturer may determine whether the dimensions of the patient's EAM are suitable for the requested device model by extracting the patient's dimensions from the DICOM file and comparing against the requested device specifications. The manufacturer may send a message to the clinician computer system indicating whether or not the extracted dimensions are suitable. Each of the steps mentioned in this implementation may be automated such that the clinician could review the dimension comparison results shortly after transmitting the DICOM file to the manufacturer. Accordingly, the workflow of the manufacturer's screening process may be reduced from days to minutes, reducing the workload and cost for clinicians and the manufacturer, and eliminating the need for a patient to return to be re-measured where a first measurement was rejected by the manufacturer. In this case, the patient may remain with the clinician until the results of the manufacturer's screening process are received. Where the measurements are rejected, the clinician may simply scan the patient again within minutes. Therefore, the burden on the patient may be reduced. In this way, the manufacturer need not produce a custom auditory canal device prior to verifying the fit of the device, thereby saving production time and cost on producing devices that do not fit.

Patients with a narrow or otherwise small EAM are generally not candidates for the Lyric, IIC, or other similar products placed deep into the EAM. In an implementation of the method of the present invention, a clinician may scan the patient's EAM, and either compare the scanned dimensions with the requirements of a particular type of auditory canal device, or send the DICOM file to the manufacturer for comparison. A comparison result may be returned quickly allowing the clinician and patient to know within minutes whether the patient is eligible for the particular type of auditory canal device.

In an implementation of the present invention, the accuracy of the scanned images is about 23.04 cm with about 576 slices and a pixel size resolution of about 0.300 mm. In another implementation of the present invention, a CBCT scanner may be used with pixel resolution size of 0.08 mm and greater. A CBCT scanner is not reliant upon physical material being inserted into the ear canal in order to produce high resolution images of the entire air. Optionally, the present invention may acquire measurements accurate to about 0.1 mm.

FIGS. 35-43 are exemplary views of images produced in accordance with aspects of the present invention showing image sizing with segmentation processing.

Figure 44:
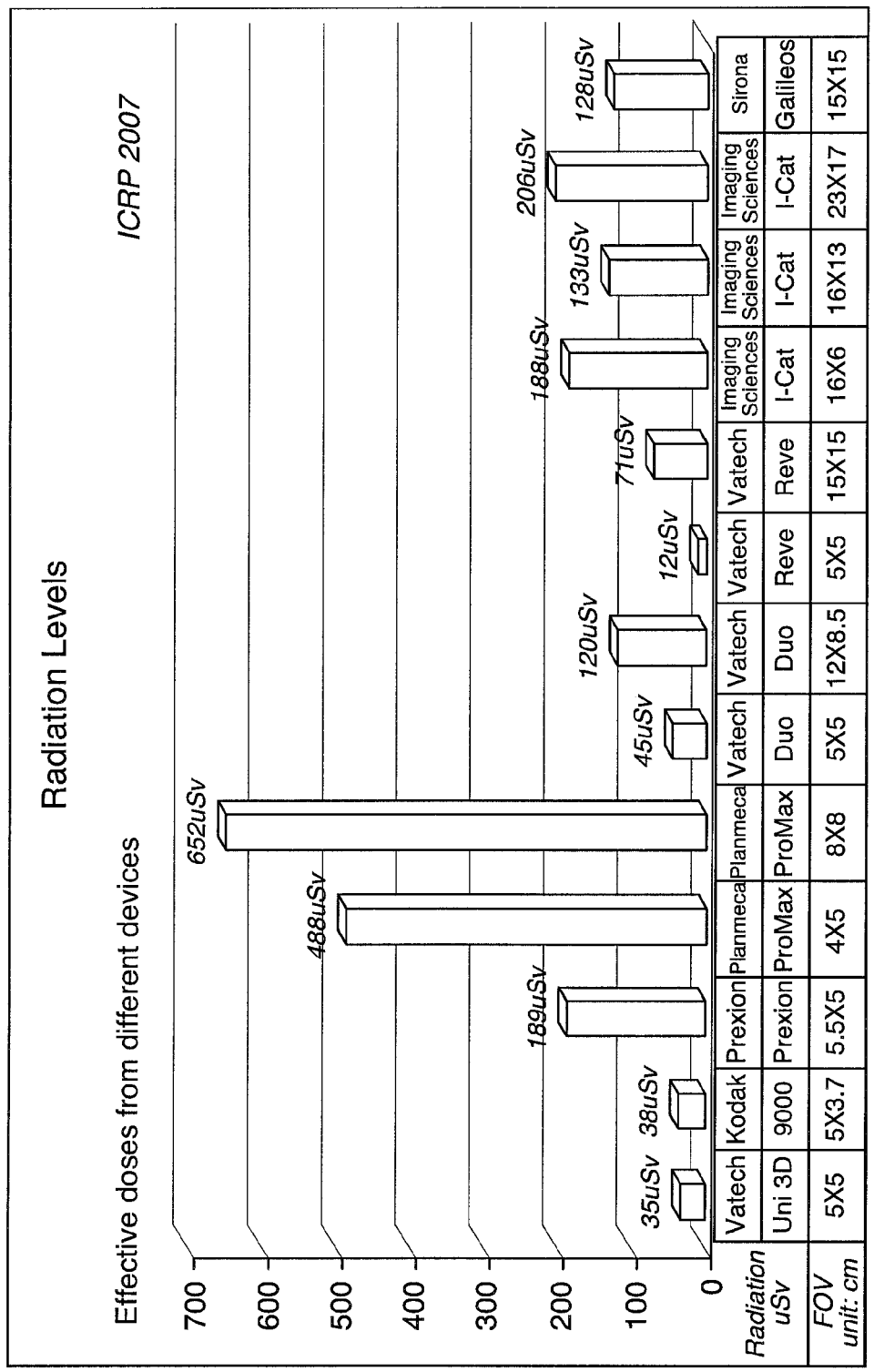
FIG. 44 is a chart showing effective radiation doses from different devices.

With respect to radiation exposure of the patient while undergoing CT or CBCT scans in accordance with an aspect of the present invention, the amount of the radiation exposure is reducible to an 8 cm×5 cm area of imaging on each side of the head. FIG. 44 is a chart showing effective radiation doses from different devices as of 2007.

Optionally, in non-limiting implementations of the present invention, one or more of the following steps may be provided:

(1) a patient case history is performed to identify factors that would contribute greater risk of harm towards the patient;

(2) otoscopic examination of the patient's pinna, EAM, and, tympanic membrane is performed;

(3) a determination is made whether the patient requires a custom auditory canal device, such that a patient only need be re-scanned where the patient's pinna, EAM, and/or tympanic membrane has changed;

(4) a determination is made whether the patient is able to remain completely still for at least 30 seconds with the patient holding a smile for a better fit and positioned correctly for the CBCT imaging for accurate results;

(5) the scanned image(s) are checked for accuracy by cross-referencing with the inspection from the otoscopic examination stage;

(6) verification that all required information has been captured, then save the image on a preferably secured network by including image date, patient's initials and other information associated with the patient that may maintain the anonymity of the patient, and specifications of left, right or both pinna and or EAM;

(7) the patient's information is cross-referenced with requirements of the selected custom product to determine suitability for the patient before transmitting the image to the product manufacturer; and (8) the 2D image data is converted to a 3D image file and transmitted to the manufacturer with a confirmation of the file sent and received by both parties.

Measuring for Facial Contouring by CT Scanning

While the invention has been described with particularity to scanning auditory canals and extracting measurements from such scans, in accordance with other aspects of the present invention, the present invention may also be applied to facial contouring. Accordingly, the same CT or CBCT imaging scanning techniques and parameters described herein with respect to auditory canal scanning may be applied to facial contouring. This may allow for a non-invasive radiologic based imaging approach for the fabrication of facial masks (e.g. nasal continuous positive airway pressure or "nCPAP"), facial cosmetic products (e.g. prosthetic noses) and for custom fitting of any type of facial strap that would involve creating a seal on the nose/mouth region with strapping on the back of the head.

Figure 46:
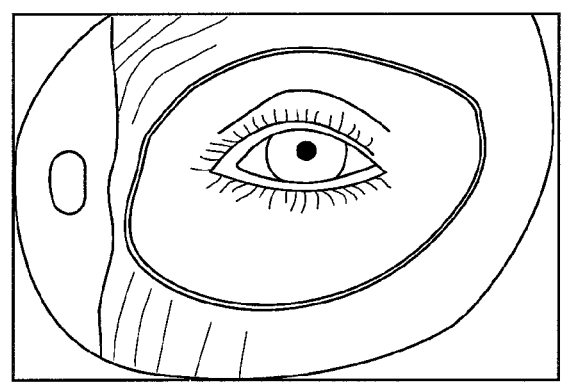
FIG. 46 illustrates an example of conventional maxillofacial prosthetics fabrication where a physical impression was taken and a plaster model was created of the defect, into which a custom eye prosthetic was fabricated.

In comparison, existing methods of obtaining a facial contour of a patient for creating a mask or prosthetic may involve obtaining an impression of the patient's face, which may typically be the technique utilized by a maxillofacial prosthetist. FIG. 46 shows an example of conventional maxillofacial prosthetics fabrication where a physical impression was taken and a plaster model was created of the defect, into which a custom eye prosthetic was fabricated. In existing methods, a physical impression may be taken with a self-setting material such that a negative mold is made of the person's face and then the negative mold is then filled with a plaster based material to create the replica of facial contour.

Figure 47:
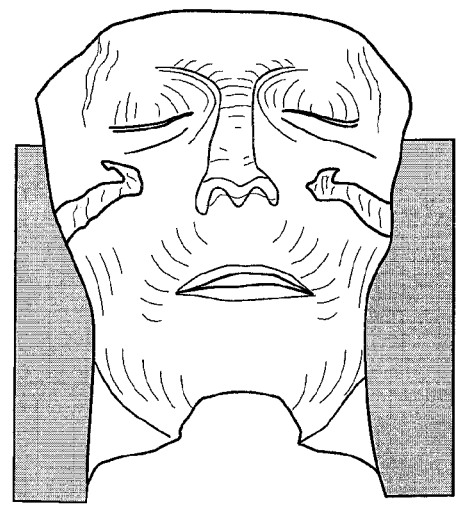
FIG. 47 illustrates a 3D segmentation of a facial contour scan including scanned auditory canals produced in accordance with aspects of the present invention.
Figure 48:
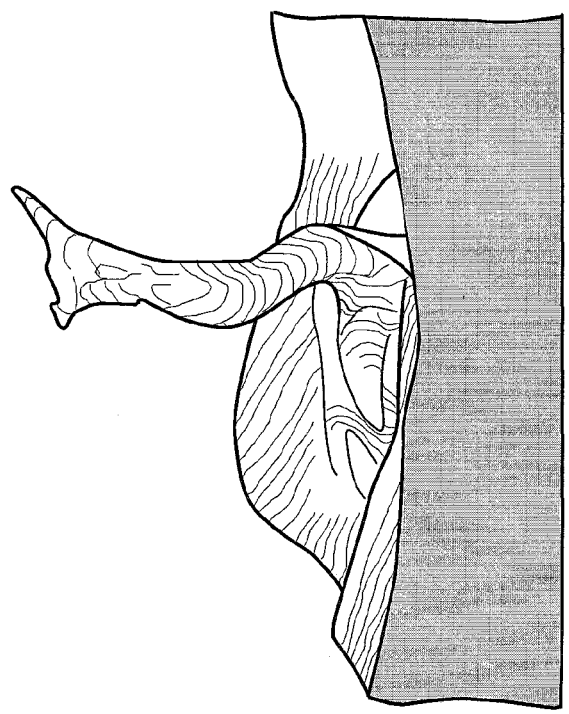
FIG. 48 illustrates a scan of an ear canal and patient ear produced in accordance with aspects of the present invention.
Figure 49:
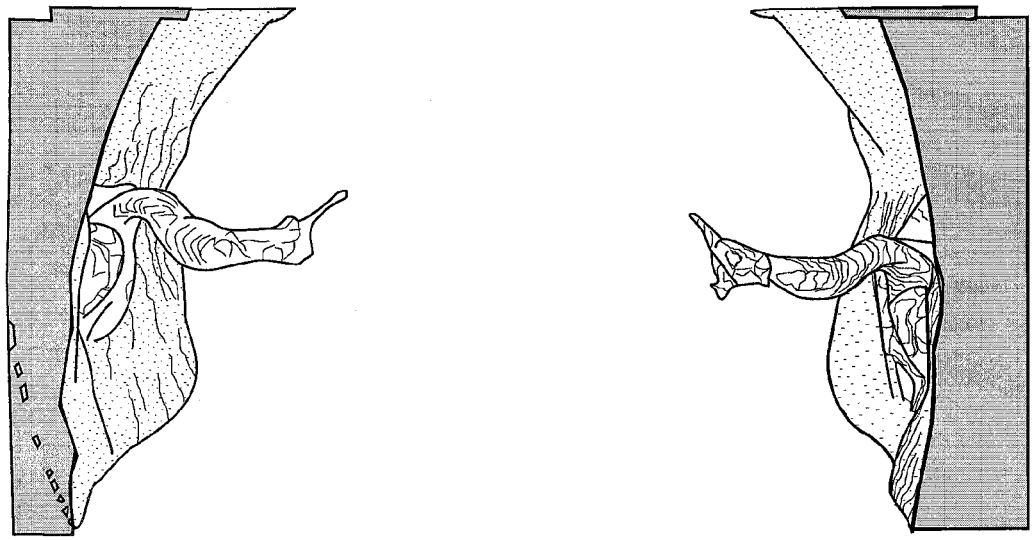
FIG. 49 illustrates a scan produced in accordance with aspects of the present invention where both ears are captured at the same time as the contour of the cheek bone and portions of the lateral face that is directly adjacent to the ear canals.

The present invention instead relies upon the use of CT and/or CBCT scans to image the head and neck region. Typical information gathering is subsurface and the focus of existing applications of imaging technology have been to gather 3D information regarding spatial relationships. This would include the position and size of tissue structures (e.g. bone, fat, muscle, fascia, teeth, etc.), lumen spaces (e.g. airways, sinuses, etc.) and their relative position and symmetry. CT imaging also captures in an unintended and non-obvious fashion, accurate surface information detail. In accordance with the present invention, CT and/or CBCT scanning may be used not to gather subsurface data but to harvest the surface data from the scans so as to create custom fitting surface products. Using the surface scan data may provide for quantification of different spatial relationships that would be very difficult to reliably measure otherwise, resulting in a precision fit of a prosthetic or mask created based on such measurements. FIG. 47 reveals the 3D segmentation of not just the ear canals as described with respect to scanning the auditory canal above, but also the facial contour that is continuous with the 3D digital impression. No physical impression material was used for the creation of this image where the forehead, nose, mouth and chin regions are all well captured. In the foreground are the two ear canals also shown. FIG. 48 shows a scan of an ear canal and patient ear made using the method of the present invention. FIG. 49 shows a scan made in accordance with the method of the present invention where both ears are captured at the same time as the contour of the cheek bone and portions of the lateral face that is directly adjacent to the ear canals.

Figure 45:
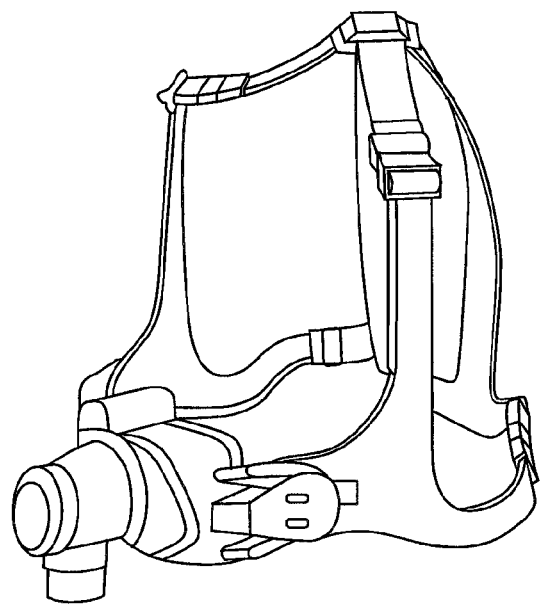
FIG. 45 illustrates an example of a commercially available non-custom nCPAP mask with a nose/mouth seal and strapping around the head region.
Figure 50:
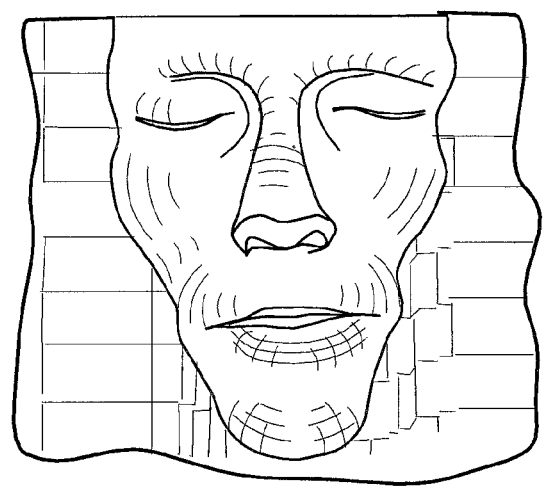
FIG. 50 illustrates a scan produced in accordance with aspects of the present invention where facial information is collected.
Figure 51:
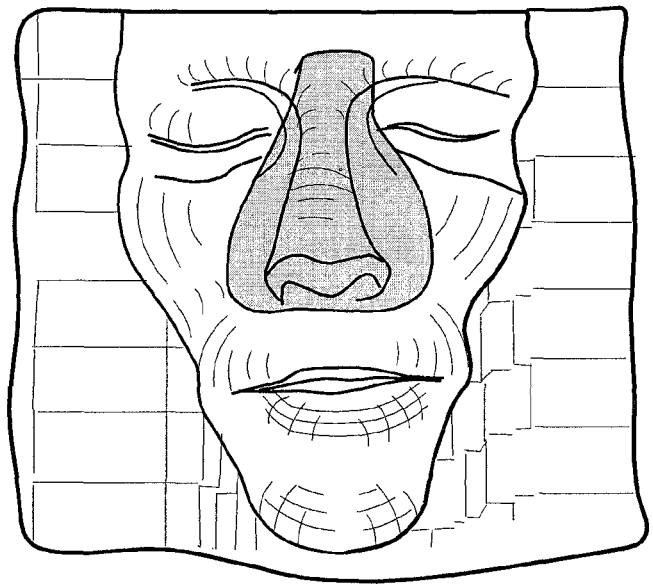
FIG. 51 illustrates selection and colourization of the nasal region of the scan of FIG. 50.
Figure 52:
FIG. 52 illustrates removal of the selected data of FIG. 51.
Figure 53:
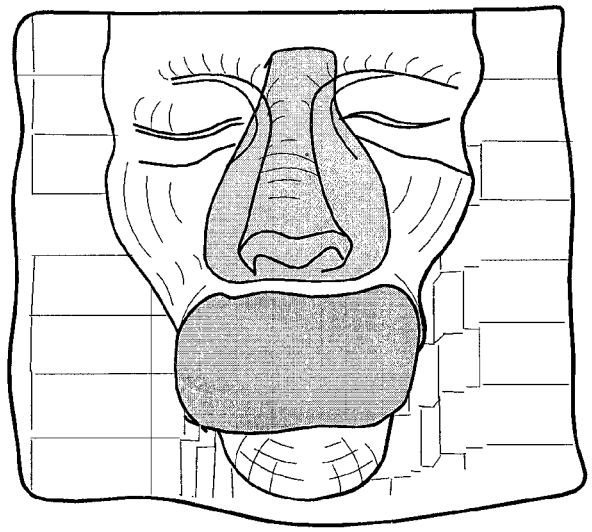
FIG. 53 illustrates removal additional areas of the scan of FIG. 50.
Figure 54:
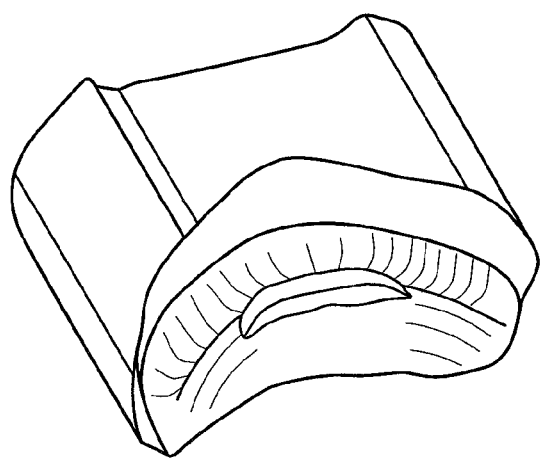
FIG. 54 illustrates the precise 3D details of the lip and mouth tissues that are captured as part of the digital impression technique in accordance with aspects of the present invention.
Figure 55:
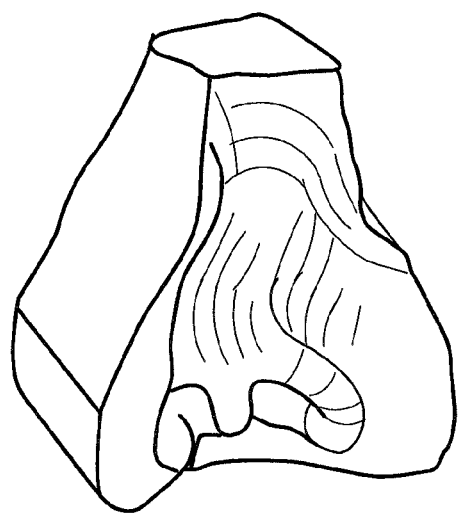
FIG. 55 illustrates a detail of the 3D contour of the nose region that can be captured as part of the digital impression technique in accordance with aspects of the present invention.
Figure 56:
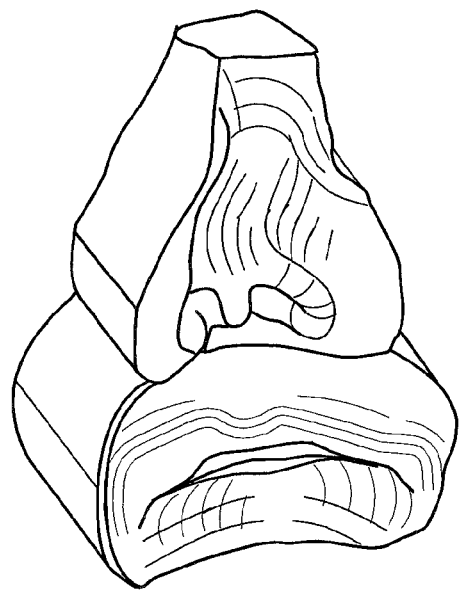
FIG. 56 illustrates that different elements of interest can be combined together to fabricate different components that fit together and function as an integral unit as part of the digital impression technique in accordance with aspects of the present invention.

For example, a custom face mask may cover the patient's nose and mouth region but then also have a custom strap that engages the back of the head. FIG. 45 shows an example of a commercially available non-custom nCPAP mask with a nose/mouth seal and strapping around the head region. The present invention may be able to extract precise measurements from the CT and/or CBCT scans so as to provide for the creation of an exacting mask fit so as to ensure a perfect air-seal around the mouth or nose with minimal pressure accumulation from strap tension or heavy mask contact. This may be particularly true of nCPAP in the treatment of obstructive sleep apnea. FIG. 50 shows a scan where facial information is also collected in accordance with aspects of the present invention. This digital mold shown covers all of the pressure points that a mask would contact as it sits on the face. Accordingly, a scan of the region shown in FIG. 50 would provide for a mask to cover any or all of the mouth, nose or both regions simultaneously. FIG. 51 illustrates selection and colourization of the nasal region alone, for example, in order to create a prosthetic of the selected region, or, for example, to remove the selected region from the image. FIG. 52 illustrates how the selected data of FIG. 51 may be virtually removed in 3D and the residual data that would, if not required, not necessarily be utilized in the fabrication of a custom nasal mask. FIG. 53 shows that additional areas of information may be harvested from the same scan. In this instance it's the mouth region separate from the nose that can be collected. FIG. 54 shows the precise 3D details of the lip and mouth tissues that are captured as part of the digital impression technique and would allow accurate fabrication of custom prosthetics for this region of the face. FIG. 55 reveals a detail of the 3D contour of the nose region that can be captured from this digital impression technique. FIG. 56 shows that different elements of interest can be combined together to fabricate different components that fit together and function as an integral unit. In this instance the nasal detail is indicated in one shade and the mouth detail is indicated in another shade.

In any event, measurement data for respective facial contours of the patient may be extracted from these scans similarly to how the measurements are extracted for the auditory canals described herein. Acceptability of the extracted measurements may be determined by the at least one computing device with reference to predetermined requirements of the at least one prosthetic and an indication of the acceptability determination may be provided by the at least one computing device contemporaneously with the measurement extracting and the scanning. The acceptability determination may also be assisted by the at least one computing device transmitting the measurements, and, optionally, an identification of the prosthetic to be created, to a computer server, such as a computer server operated by a prosthetic manufacturer. The measurements may also be transmitted to the computer server to create a prosthetic with the precise measurements provided. The at least one computer server may analyze the measurements to determine their acceptability (e.g. whether the measurements are complete or of a sufficient level of detail to produce the prosthetic), and transmit the acceptability determination to the at least one computing device. If the measurements are not acceptable, additional or replacement scanning may be performed without the patient having to leave and return another time. In this way, determining acceptability of measurements for a facial prosthetic may also be performed relatively contemporaneously with the scanning and measurement extracting.

General

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

Figure 57:
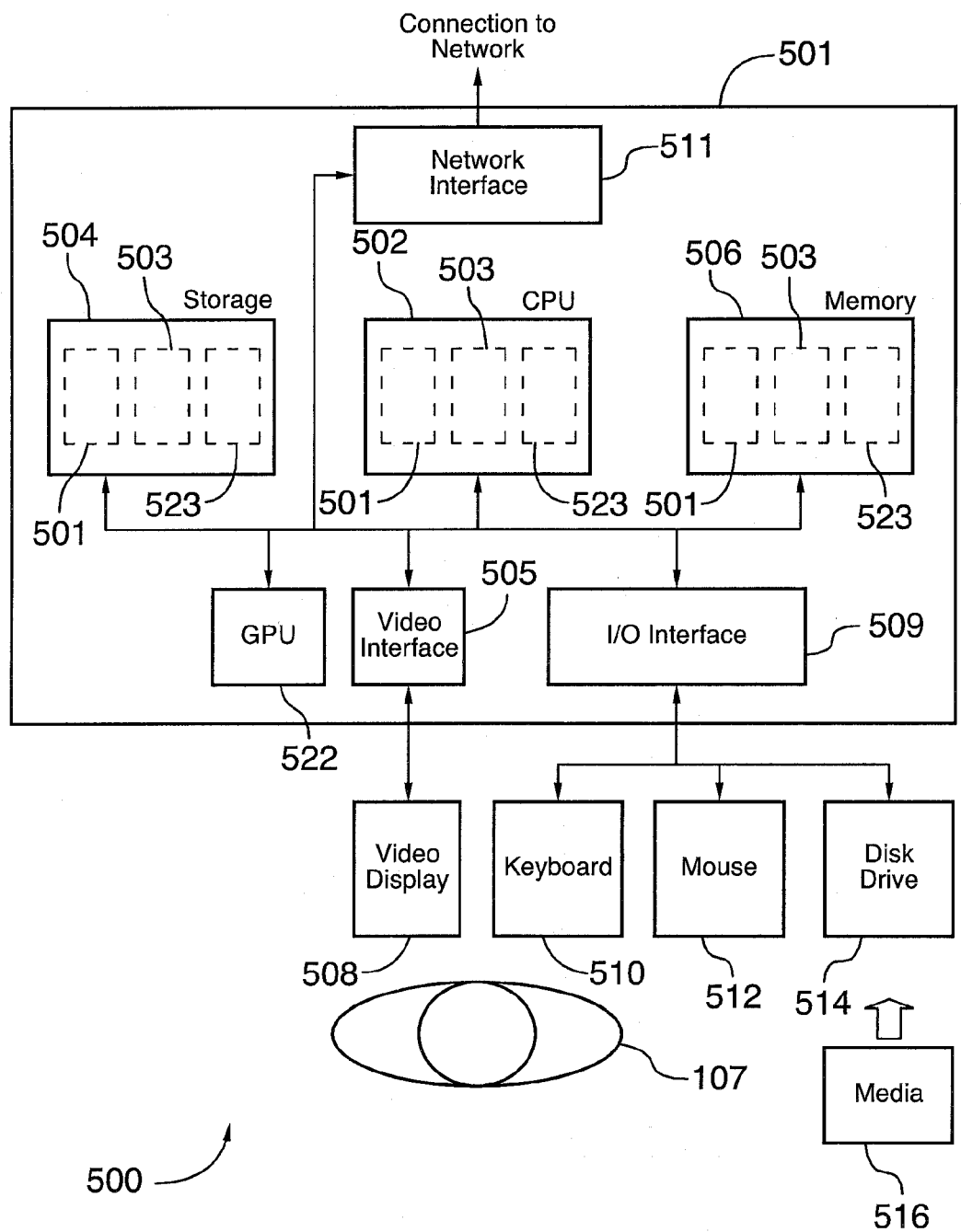
FIG. 57 illustrates an embodiment of the system of the present invention.

The present system and method may be practiced in various embodiments. A suitably configured computer device, and associated communications networks, devices, software and firmware may provide a platform for enabling one or more embodiments as described above. By way of example, FIG. 57 shows a generic computer device 500 that may include a central processing unit ("CPU") 502 connected to a storage unit 504 and to a random access memory 506. The CPU 502 may process an operating system 501, application program 503, and data 523. The operating system 501, application program 503, and data 523 may be stored in storage unit 504 and loaded into memory 506, as may be required. Computer device 500 may further include a graphics processing unit (GPU) 522 which is operatively connected to CPU 502 and to memory 506 to offload intensive image processing calculations from CPU 502 and run these calculations in parallel with CPU 502. An operator 507 may interact with the computer device 500 using a video display 508 connected by a video interface 505, and various input/output devices such as a keyboard 510, mouse 512, and disk drive or solid state drive 514 connected by an I/O interface 509. In known manner, the mouse 512 may be configured to control movement of a cursor in the video display 508, and to operate various graphical user interface (GUI) controls appearing in the video display 508 with a mouse button. The disk drive or solid state drive 514 may be configured to accept computer readable media 516. The computer device 500 may form part of a network via a network interface 511, allowing the computer device 500 to communicate with other suitably configured data processing systems (not shown).

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:

1. A method performed by at least one computing device, the method comprising:

extracting measurements of at least one auditory canal from at least one computerized imaging scan of the at least one auditory canal devoid of physical measurement aids;

partitioning the at least one computerized imaging scan into a plurality of image segments;

locating common elements of the auditory canal shown in the plurality of image segments;

mapping the plurality of image segments to a 3D co-ordinate system based at least partly on the located common elements;

rendering the mapping plurality of image segments as at least one 3D image;

determining acceptability for at least one auditory canal device at least partly by comparing the measurements of the at least one auditory canal with predetermined measurements of the at least one auditory canal device; and providing an indication of the acceptability determination contemporaneously with the measurement extracting, wherein the at least one computerized imaging scan is produced by at least one computed tomography ("CT") scanner scanning the at least one auditory canal, with the indication of the acceptability determination being provided contemporaneously with the scanning.

2. The method of claim 1 wherein the at least one auditory canal comprises a tympanic membrane within the at least one auditory canal, a first bend of the at least one auditory canal, and a second bend of the at least one auditory canal between the first bend and the tympanic membrane, the extracted measurements of the at least one auditory canal comprising measurements of the at least one auditory canal between the second bend and the tympanic membrane.

3. The method of claim 1 wherein the at least one auditory canal is devoid of physical measurement aids including auditory canal impression materials and radiographic markers during the scanning.

4. The method of claim 1 wherein the CT scanner comprises a cone beam computed tomography ("CBCT") scanner.

5. The method of claim 1 wherein the scanning comprises the CT scanner orbiting a head of a patient comprising the at least one auditory canal in a predefined path.

6. The method of claim 5 wherein the at least one auditory canal comprises an auditory canal for each of two ears of the patient, and the predefined path provides for scanning each auditory canal prior to the determining acceptability.

7. The method of claim 1 comprising:

transmitting the measurements and an identification of the at least one auditory canal device to at least one computer server over a communications network;

receiving data from the computer server over the communications network, the data including a determination of the extracted measurement acceptability for use in the determining acceptability for the at least one auditory canal device; and providing an indication of whether additional scanning is required in accordance with the extracted measurement acceptability determination.

8. The method of claim 7 comprising, in accordance with the received data, the CT scanner re-scanning the at least one auditory canal to produce at least one replacement computerized imaging scan for the at least one computerized imaging scan.

9. The method of claim 1 wherein the locating common elements comprises identifying at least one common element based at least partly on patient skin density data captured in the at least one computerized imaging scan.

10. The method of claim 1 comprising formatting the measurements into a data file in accordance with a standardized computerized file format.

11. The method of claim 10 comprising transmitting the data file and an identification of the at least one auditory canal device to at least one computer server over a communications network; and wherein the determining acceptability is based at least partly on a determination of acceptability received from the at least one computer server.

12. The method of claim 1 comprising identifying common elements in the 3D image located beyond the tympanic membrane in the at least one auditory canal; and removing the identified common elements from the 3D image.

13. The method of claim 1 comprising transmitting the measurements and an identification of the at least one auditory canal device to at least one computer server over a communications network; and wherein the determining acceptability is based at least partly on a determination of eligibility received from the at least one computer server.

14. The method of claim 13 comprising formatting the measurements into a data file in accordance with a standardized computerized file format, the transmitting comprising transmitting the data file to the at least one computer server.

15. A system comprising at least one computer processor coupled to a non-transitory computer-readable medium or media comprising computer-executable instructions configured to cause the at least one computer processor to:
extract measurements of at least one auditory canal from at least one computerized imaging scan of the at least one auditory canal devoid of physical measurement aids;
determine acceptability for at least one auditory canal device at least partly by comparing the measurements of the at least one auditory canal with predetermined measurements of the at least one auditory canal device; and
provide an indication of the acceptability determination contemporaneously with the measurement extracting.

16. The system of claim 15 comprising at least one computed tomography ("CT") scanner coupled to the at least one computer processor; wherein the at least one computerized imaging scan is produced by the CT scanner and the indication of the acceptability determination is provided contemporaneously with the scanning.

17. The system of claim 16 wherein the instructions are configured to cause the at least one computer processor to control the CT scanner to orbit a head of a patient comprising the at least one auditory canal in a predefined path to produce the at least one computerized imaging scan.

18. The system of claim 15 wherein the instructions are configured to cause the at least one computer processor to:
transmit the measurements and an identification of the at least one auditory canal device to at least one computer server over a communications network;
receive data from the computer server over the communications network, the data including a determination of the extracted measurement acceptability for use in the determining eligibility acceptability of the at least one auditory canal device; and
provide an indication of whether additional scanning is required in accordance with the extracted measurement acceptability determination.

19. A method performed by at least one computing device, the method comprising:
scanning at least one facial contour of a person at least partly by using at least one computer tomography ("CT") scanner coupled to the at least one computing device;
extracting measurements of the at least one facial contour from at least one computerized imaging scan of the at least one facial contour produced by the at least one CT scanner;
determining acceptability of the extracted measurements for production of at least one prosthetic based at least partly on predetermined requirements of the at least one prosthetic; and
providing an indication of the acceptability determination contemporaneously with the measurement extracting and the scanning.

20. A system comprising at least one computer processor coupled to a non-transitory computer-readable medium or media comprising computer-executable instructions configured to cause the at least one computer processor to:
scan at least one facial contour of a person at least partly by using at least one computer tomography ("CT") scanner coupled to the at least one computing device;
extract measurements of the at least one facial contour from at least one computerized imaging scan of the at least one facial contour produced by the at least one CT scanner;
determine acceptability of the extracted measurements for production of at least one prosthetic based at least partly on predetermined requirements of the at least one prosthetic; and
provide an indication of the acceptability determination contemporaneously with the measurement extracting and the scanning.

* * * * *